(12) United States Patent
Silberberg et al.

(10) Patent No.: US 7,403,282 B2
(45) Date of Patent: Jul. 22, 2008

(54) COHERENTLY CONTROLLED NONLINEAR RAMAN SPECTROSCOPY AND MICROSCOPY

(75) Inventors: Yaron Silberberg, Lehavim (IL); Nirit Dudovich, Mazkeret Batya (IL); Dan Oron, Rehovot (IL)

(73) Assignee: Yeda Research and Development Company Ltd., Rehovot (IL)

( * ) Notice: Subject to any disclaimer, the term of this patent is extended or adjusted under 35 U.S.C. 154(b) by 0 days.

(21) Appl. No.: 11/778,311

(22) Filed: Jul. 16, 2007

(65) Prior Publication Data

US 2007/0291264 A1 Dec. 20, 2007

Related U.S. Application Data

(63) Continuation of application No. 10/353,063, filed on Jan. 29, 2003, now Pat. No. 7,256,885.

(51) Int. Cl.
*G01J 3/44* (2006.01)
*H01S 3/10* (2006.01)
*H01S 3/00* (2006.01)

(52) U.S. Cl. .................... 356/301; 372/25; 372/109
(58) Field of Classification Search ................ None
See application file for complete search history.

(56) References Cited

U.S. PATENT DOCUMENTS

| | | | |
|---|---|---|---|
| 3,782,828 A | 1/1974 | Alfano et al. |
| 4,077,719 A | 3/1978 | Barrett et al. |
| 4,084,100 A | 4/1978 | Begley et al. |
| 4,277,760 A | 7/1981 | Eckbreth |
| 4,405,237 A | 9/1983 | Manuccia et al. |
| 4,512,660 A | 4/1985 | Goldberg |
| 4,619,528 A | 10/1986 | Genack et al. |
| 5,095,487 A | 3/1992 | Meyerhofer et al. |
| 5,303,710 A | 4/1994 | Bashansky et al. |
| 5,689,362 A | 11/1997 | Kadota |
| 6,108,081 A | 8/2000 | Holtom et al. |
| 6,175,437 B1 | 1/2001 | Diels et al. |
| 6,327,068 B1 | 12/2001 | Silberberg et al. |
| 7,092,086 B2 | 8/2006 | Knebel |

(Continued)

FOREIGN PATENT DOCUMENTS

WO     02/06778 A1    1/2002

(Continued)

OTHER PUBLICATIONS

Cheng J-X et al.: Polarization Cohnerent Anit-Strokes, Raman Scattering Microscopy, Optics Letters, Optical Society of America, Washington, US vol. 26, No. 17, Sep. 1, 2001, pp. 1341-1343.

(Continued)

*Primary Examiner*—Gregory J. Toatley, Jr.
*Assistant Examiner*—Gordon J Stock, Jr.
(74) *Attorney, Agent, or Firm*—Browdy and Neimark

(57) ABSTRACT

A method and system are presented for producing an output coherent anti-stokes Raman scattering (CARS) signal of a medium. The method comprises generation of a unitary optical excitation pulse that carries a pump photon, a Stokes photon and a probe photon; and inducing a CARS process in the medium by exciting the medium by the at least one such unitary optical excitation pulse.

39 Claims, 13 Drawing Sheets

U.S. PATENT DOCUMENTS

| | | |
|---|---|---|
| 7,106,436 B1 | 9/2006 | Gord et al. |
| 2002/0172243 A1 | 11/2002 | Ono et al. |
| 2003/0099264 A1 | 5/2003 | Dantus et al. |
| 2003/0160955 A1 | 8/2003 | Xie et al. |
| 2004/0065845 A1 | 4/2004 | Seyfried |
| 2004/0113059 A1 | 6/2004 | Kawano et al. |

FOREIGN PATENT DOCUMENTS

| | | |
|---|---|---|
| WO | 02/48660 A1 | 6/2002 |

OTHER PUBLICATIONS

Meschulach D et al: "Coherent Quantum Control of Multiphoton Transitions by Shaped Ultrashort Optical Pulses" Physical Review A, vol. 60, No. 2. 1999, pp. 1287-1292.

Meschulach D et al: "Coherent Quantum Control of Two-Photon Transitions by a Femtosecond Laser Pulse", Nature, vol. 396, 1998, pp. 239-242.

Silberberg Y et al: "New Methods in Femtosecond in Multiphoton Microscopy", Proc. SPIE: Microphoton Microscopy in the Biomediacal Sciences III, vol. 4963, No. 1 Jan. 26-28, 2003, pp. 209-222, San Jose, CA.

Oudar J-L et al: "Polarization Sensitive Coherent Anti-Strokes Raman Spectroscopy", Applied Physics Letters, American Institute of Physics, New York, US vol. 34, No. 11, Jun. 1, 1979, pp. 758-760.

Leonhardt et al.; "Terahertz Quantum Beats in Molecular Liquids"; Chemical Physics Letters; Jan. 30, 1987; pp. 373-377; vol. 133; No. 5; Elsevier Science Publishers B.V.

Zumbusch et al.; "Three-Dimensional Vibrational Imaging by Coherent Anti-Stokes Raman Scattering"; Physical Review Letters; May 17, 1999; pp. 4142-4145; vol. 82, No. 20; The American Physical Society, 1999.

Hashimoto et al.; "Molecular vibration imaging in the fingerprint region by use of coherent anti-Stokes Raman scattering microscopy with a collinear configuration"; Optics Letters; Dec. 15, 2000; pp. 1768-1770, vol. 25, No. 24; Optical Society of America, 2000.

Volkmer et al.; "Time-resolved coherent anti-Stokes Raman scattering microscopy: Imaging based on Raman free induction decay"; Applied Physics Letters; Mar. 4, 2002, pp. 1505-1507, vol. 80, No. 9; American Institute of Physics, 2002.

Schrader; Infrared and Raman Spectroscopy, Methods and Applications; pp. 172-183, VCH Verlagsgesellschaft mbH, 1995.

Oron et al.; "Quantum control of coherent anti-Stokes Raman process"; Physical Review A; pp. 043408-1-043408-4, vol. 65; The American Physical Society, 2002.

Dan Oron et al.; "Narrow-Band Coherent Anti-Stokes Raman Signals from Broad-Band Pulses"; Physical Review Letters; Feb. 11, 2002, pp. 063004-1-063004-4, vol. 88, No. 6; The American Physical Society, 2002.

A. M. Weiner; "Femtosecond pulse shaping using spatial light modulators"; Review of Scientific Instruments; May 2000, pp. 1929-1960, vol. 71, No. 5; American Institute of Physics, 2000.

Brixner et al.; "Femtosecond polarization pulse shaping"; Optics Letters; Apr. 15, 2001; pp. 557-559, vol. 26, No. 8; Optical Society of America, 2001.

Brixner et al.; "Generalization and characterization of polarization-shaped femtosecond laser pulses"; Applied Physics B, Laser and Optics; Jul. 5, 2002; pp. S133-S144; Springer-Verlag, 2002.

Dudovich et al.; "Single-pulse coherently controlled nonlinear Raman spectroscopy and microscopy"; letters to nature; Aug. 1, 2002; pp. 512-514, vol. 418; Nature Publishing Group, 2002.

Dudovich et al, "Single-pulse Coherent Anti-Stokes Raman Spectroscopy in the Fingerprint Spectral Region", Journal of Chemical Physics, May 22, 2003, pp. 9208-9215, vol. 118, No. 20.

Oron et al, "Femtosecond Phase-and-Polarization Control for Background-Free Coherent Anti-Stokes Raman Spectroscopy", Physical Review Letters, May 30, 2003, vol. 90, No. 21, pp. 213902-1-213902-4.

Oron et al, "Single-Pulse Phase-Contrast Nonlinear Raman Spectroscopy", Physical Review Letters, Dec. 30, 2002, vol. 89, No. 27, pp. 273001-1-273001-4.

COHERENTLY CONTROLLED NONLINEAR RAMAN SPECTROSCOPY AND MICROSCOPY

FIELD OF THE INVENTION

The present invention relates to Raman spectroscopy and microscopy, and in particular, to coherent anti-stokes Raman spectroscopy and microscopy.

BACKGROUND OF THE INVENTION

In coherent nonlinear spectroscopy, the sample is probed by measuring processes of energy exchange between photons interacting with the sample. One of the most common nonlinear spectroscopy methods is coherent anti-stokes Raman scattering (CARS), a coherent four-wave mixing process involving the generation of a coherent vibration in the probed medium. In CARS, three laser photons, a pump photon ($\omega_p$) a probe photon ($\omega_{pr}$) and the Stokes photon ($\omega_s$), overlap in the medium under investigation. By nonlinear interaction with the molecules a fourth coherent photon ($\omega_{AS}$) with the anti-Stokes frequency $\omega_{AS}=\omega_p-\omega_s+\omega_{pr}$ is generated.

The CARS process can be visualized in a molecular energy level diagram as depicted in FIG. 1, where $|i\rangle$ and $|\beta\rangle$ are molecular rovibrational states, and $|\alpha\rangle$ and $|\beta\rangle$ are virtual levels. Resonant enhancement of the CARS process occurs when the frequency difference $\Omega_R=\omega_p-\omega_s$ coincides with a vibrational level of the medium.

The CARS process, as a coherent scattering process, has to fulfill a phase matching condition, which is equivalent to momentum conservation of the photons involved. With the wave vectors of the pump photon ($k_P$), the probe photon ($k_{pr}$) and the Stokes photon ($k_S$), the wave vector of the Raman signal can be obtained by $$k_{AS}=k_{pr}+(k_P-k_S) \text{ or } k_P+k_{pr}=k_{AS}+k_S.$$

In general, there are two conventional different techniques utilizing a multi-beam excitation scheme for measuring a CARS spectrum, as disclosed, for example, in U.S. Pat. Nos. 4,077,719; 4,084,100; 4,405,237; and 4,512,660; and in WO 02/48660.

According to the first technique, the so-called scanning CARS, two narrow bandwidth lasers at $\omega_p$ and at $\omega_s$ (having spectral width of the order of the typical linewidth of Raman levels, i.e., 1 cm$^{-1}$) are tuned over the Raman resonances of the probed species to generate a signal at $2\omega_p-\omega_s$ (in this case $\omega_{pr}=\omega_s$). The spectral resolution of this technique is mainly determined by the bandwidth of the applied laser sources.

According to the second technique, broadband or multiplex CARS, a broadband Stokes beam (spectral width typical 100-1000 cm$^{-1}$) can be used to excite several Raman transitions under investigations simultaneously. The use of a narrow band probe and a broadband Stokes beam enables simultaneous measurement of the entire band of the Raman spectrum (see, for example, "*Infrared and Raman Spectroscopy*," edited by B. Schrader, VCH, Weinheim, 1995). The spectral resolution of this technique is usually achieved by using a monochromator and a multichannel detection system. Thus, one laser shot is utilized to measure the entire CARS spectrum.

Another possibility to obtain multiplex CARS spectra is to use a time-resolved CARS scheme. In this technique, two relatively broadband exciting pulses are used for simultaneously populating several Raman levels. The spectral data is obtained by measuring the interference pattern of the CARS signal from a third, delayed broadband probe pulse (see, for example, an article of Leonhardt et al., published in Chem. Phys. Lett., 1987, V. 133, P. 373).

Coherent Raman processes have become a valuable tool in the past few decades in femtosecond time-resolved spectroscopy, as well as in combustion studies and condensed-state spectroscopy. For example, Leonhardt et aL describes in Chem. Phys. Lett. 1987, V. 133, P. 373 the measurements of the energy difference and the lifetimes of two (or more) Raman levels by Fourier-decomposing the quantum beats of the CARS signal using femtosecond pulses. This scheme has been recently used to analyze the energy-level diagram of complex molecules.

CARS has recently become a favorable technique for nonlinear depth-resolved microscopy (see, for example, U.S. Pat. No. 6,108,081; WO 02/06778; and scientific articles Zumbusch et al., Phys. Rev. Lett., 1999, V. 82, P. 4142; Hashimoto et al., Opt. Lett., 2000, V. 25, P. 1768; and Volkmer at al., Applied Phys. Lett., 2002, V. 80, P. 1505). CARS microscopy has the potential, for example, for studying live biological specimens while gathering three-dimensional information on their molecular constitution. However, the these CARS microscopes also require two or three narrow-band sources that must be all tightly synchronized and also tunable within the Raman energy range.

It should be appreciated that the signal of CARS (being a result of a nonlinear process) is stronger with short intense pulses. However, the femtosecond CARS techniques suffer from two major difficulties. First, there is an increased strong background signal typically due to the electronic contributions to the third-order susceptibility, both from the sample and from the surrounding medium (i.e., solvent). The second difficulty is associated with a lack of selectivity between neighboring energy levels, due to the large bandwidth of the pulses.

These problems can be solved by coherent quantum control methods. The concept of coherent quantum control of a quantum system is based on the achievement of constructive interference between different quantum paths leading to a desirable outcome, while interfering destructively with paths leading to other outcomes. While schemes of coherent control may involve excitations by continuous waves, most available techniques are also known which involve ultrashort optical pulses. With the recent progress in ultrafast optics, it is now possible to shape ultrashort signals with desired spectral shapes (see, for example, U.S. Pat. No. 6,327,068 assigned to the assignee of the present application).

The inventors of the present invention have recently shown how coherent control techniques can be exploited to improve the CARS spectroscopy employing three femtosecond pulses related to the pump, Stokes and probe beams, respectively. Two approaches have been described for controlling the CARS process. According to the first approach ("*Quantum Control of Coherent anti-Stokes Raman Processes*" by Oron et al., published in Phys. Rev. A, 2002, V 65, P. 43408), a periodic phase modulation is used to control the population induced by broadband pulses. By shaping both the pump and the Stokes pulses with an appropriate spectral phase function, the nonresonant CARS background has been greatly reduced. This technique also allows for exciting just one out of many vibrational levels, even when all of them are within the spectral bandwidth of the excitation pulses. According to the second approach ("*Narrow-Band Coherent Anti-Stokes Raman Signals from Broad-Band Pulses*" by Oron et al., published in Phys. Rev. Lett., 2002, V. 88, P. 63004), only the probe pulse is shaped, thereby enabling enhancement of the resolution of the measured CARS spectrum. The achieved spectral resolution becomes significantly better than the bandwidth of the readout pulse. In particular, by tailoring the phase of a 100 femtosecond probe pulse, a narrow-band CARS spectroscopy resonant signal has been obtained with a width of less than 15 cm$^{-1}$, which is an order of magnitude narrower than the CARS signal from an unshaped, transform limited pulse (all frequency components having the same phase).

SUMMARY OF THE INVENTION

There is a need in the art to facilitate coherent anti-stokes Raman scattering (CARS) spectroscopy and microscopy by providing a novel method and system for producing an exciting signal to induce a CARS process in a medium.

The main idea of the present invention consists of inducing a CARS process in a medium (i.e., providing a CARS spectrum of the medium) by exciting the medium with a single pulse carrying a pump photon, a Stokes photon and a probe photon. In other words, the technique of the present invention provides for supplying three interacting photons (the pump photon, Stokes photon and probe photon) by the same unitary excitation pulse. This enables the system operation with a single laser source generating a transform limited femtosecond pulse. The present invention provides various coherent-control techniques consisting of shaping the transform limited pulse broadband pulse (carrying a pump photon, a Stokes photon and a probe photon) to produce a unitary optical excitation pulse enabling identification of a CARS signal induced by this pulse from any other optical signal.

The present invention provides for designing a single-pulse CARS spectrometer or microscope free of the two aforementioned difficulties, and for achieving high spectral resolutions and diminishing the detrimental effects of the nonresonant background.

The concept of the present invention for performing a nonlinear optical interaction with a matter in a single coherently controlled pulse offers a promising alternative to the conventional multi-beam nonlinear systems in use today.

Thus, according to one aspect of the present invention, there is provided a method for producing an output coherent anti-stokes Raman scattering (CARS) signal of a medium, the method comprising: (i) producing a unitary optical excitation pulse that carries a pump photon, a Stokes photon and a probe photon; and (ii) inducing a CARS process in the medium by exciting the medium by the at least one unitary optical excitation pulse.

The unitary optical excitation pulse carrying the pump, Stokes and probe photons is produced by generating a transform limited optical pulse carrying the pump, Stokes and probe photons; and applying a predetermined shaping to the transform limited optical pulse.

The shaping of the transform limited optical pulse may comprise blocking wavelengths shorter than a predetermined wavelength in said pulse. This predetermined wavelength is defined by a spectral bandwidth in which the output CARS signal is likely to occur.

The shaping of the transform limited optical pulse may comprise assigning a desired phase to each wavelength component of the transform limited optical pulse. The assigning of the desired phase is preferably carried out is addition to the blocking of wavelengths shorter than the predetermined wavelength. The assigning of the desired phase preferably includes modulating a spectral phase of the transform limited optical pulse by using a desired spectral phase function. The desired spectral phase function may be a periodic function, or may be formed by at least one phase gate having a bandwidth substantially narrower than the bandwidth of the unitary excitation pulse to be produced. The phase gate may for example be a $\pi$ phase gate, e.g., with the bandwidth in the range of about 0.5 nm to 3 nm. The $\pi$ phase gate is preferably spectrally located in the vicinity of a short wavelength end of the excitation pulse to be produced.

The above shaping can be implemented by passing the transform limited pulse through a Spatial Light Modulator (SLM).

Alternatively or additionally to the phase modulation, the shaping may comprise application of polarization control to the transform limited pulse consisting of 90 degree polarization rotation of predetermined wavelengths of the pulse. This results in that the inp0ut transform limited pulse is split into a broadband pump component and a narrow-band probe component having substantially orthogonal polarizations.

According to another aspect of the invention, there is provided a pulse creation method for use in coherent anti-stokes Raman scattering (CARS) spectroscopy or microscopy, the method comprising: utilizing a single laser operable to generate a transform limited optical pulse carrying a pump photon, a Stokes photon and a probe photon, and applying a predetermined shaping to the transform limited optical pulse to produce a unitary optical excitation pulse.

According to yet another aspect of the invention, there is provided a method for coherent anti-stokes Raman scattering (CARS) spectroscopy of a medium constituted of molecules capable of producing an output CARS signal, comprising:

(a) producing at least one unitary optical excitation pulse that carries a pump photon, a Stokes photon and a probe photon;

(b) focusing said at least one unitary optical excitation pulse onto the medium, thereby exciting the medium to produce the output CARS signal of the molecules; and (c) measuring said output CARS signal.

According to yet another aspect of the invention, there is provided a method for coherent anti-stokes Raman scattering (CARS) microscopy of a target material constituted of molecules producing an output CARS signal, the method comprising:

producing at least one unitary optical excitation pulse that carries a pump photon, a Stokes photon and a probe photon;

focusing said at least one unitary optical excitation pulse onto the medium, thereby exciting the medium to produce the output CARS signal of the molecules;

providing a relative displacement between the medium and the exciting beam to thereby enable scanning of the medium by the unitary excitation pulse beam.

The invention according to its yet another aspect provides a system for use in measuring an output coherent anti-stokes Raman scattering (CARS) signal of a medium, the system comprising a single laser operable to generate at least one transform limited optical pulse carrying a pump photon, a Stokes photon and a probe photon, and a programmable pulse shaper for receiving the transform limited optical pulse and shaping it to produce a unitary optical excitation pulse.

There has thus been outlined, rather broadly, the more important features of the invention in order that the detailed description thereof that follows hereinafter may be better understood. Additional details and advantages of the invention will be set forth in the detailed description, and in part will be appreciated from the description, or may be learned by practice of the invention.

BRIEF DESCRIPTION OF THE DRAWINGS

In order to understand the invention and to see how it may be carried out in practice, a preferred embodiment will now be described, by way of non-limiting example only, with reference to the accompanying drawings, in which.

DETAILED DESCRIPTION OF SPECIFIC EMBODIMENTS

Figure 1:
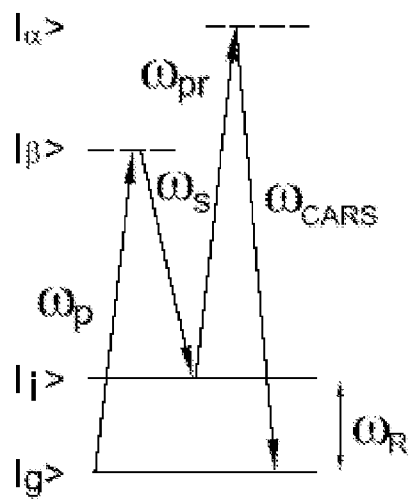
FIG. 1 is an energy level diagram of the typical CARS process.

The present invention provides a method and a CARS system such as spectrometer or microscope carrying out this method based on inducing the entire CARS process by producing a single (unitary) ultrashort optical excitation pulse that supplies all three photons (the pump photon, Stokes photon and probe photon) required for the CARS process.

The principles and operation of the CARS spectrometry and microscopy according to the present invention may be better understood with reference to the drawings and the accompanying description, it being understood that these drawings and examples in the description are given for illustrative purposes only and are not meant to be limiting. The same reference numerals will be utilized for identifying those components which are common in the CARS spectrometer and microscope systems shown in the drawings throughout the present description of the invention.

It should be noted that the inducing of the entire CARS process by a single excitation pulse is feasible when the pulse duration is shorter than the vibrational period of the molecules of the medium under investigation. For example, a length of this excitation pulse can be in a femtosecond range. In this case, the CARS signal is produced by an intra-pulse four-wave mixing process. Each of the different components of the CARS signal is the resultant of the interference of all the quantum paths that contribute to the nonlinear polarization process.

It should also be noted that inducing the CARS process with a single excitation pulse is associated with several inherent difficulties. First of all, a technical difficulty arises from the partial spectral overlap between the spectral bands of the excitation pulse and the CARS signal, which can be orders of magnitude weaker than the pulse signal.

This difficulty, according to one embodiment of the invention, can be overcame by means of a partial blocking of the excitation pulse spectrum in the range of the expected CARS signal, and an appropriate spectral filtering of the measured CARS signal.

Moreover, if a medium is excited by a single transform limited pulse (i.e., a pulse in which all frequency components have the same phase), then the CARS process can encounter the following difficulties:

One of the difficulties arises from the fact that all vibrational levels having the energy within the bandwidth of the transform limited pulse are excited. As a result, the spectral resolution of the CARS signal is limited by the excitation pulse bandwidth.

Another known difficulty, which is common to all CARS techniques utilizing femtosecond pulses and is therefore relevant also to the single-pulse CARS spectrometer and method of the present invention, results from a strong nonresonant background signal. As the bandwidth of the excitation pulse is increased (in other words, as the shorter excitation pulse having higher peak intensity is used), the magnitude of the background signal increases much more rapidly than the resonant CARS signal. The nonresonant background signal thus can be detrimental to the ability to spectrally resolve resonant transitions.

The present invention provides for eliminating the above difficulties by applying a quantum coherent control technique to the transform limited optical pulse. According to the invention, the quantum coherent control is achieved by means of a predetermined shaping of the transform limited pulse to produce a unitary optical excitation pulse that enables identification of a CARS signal induced by this pulse from any other optical signals.

Figure 2A:
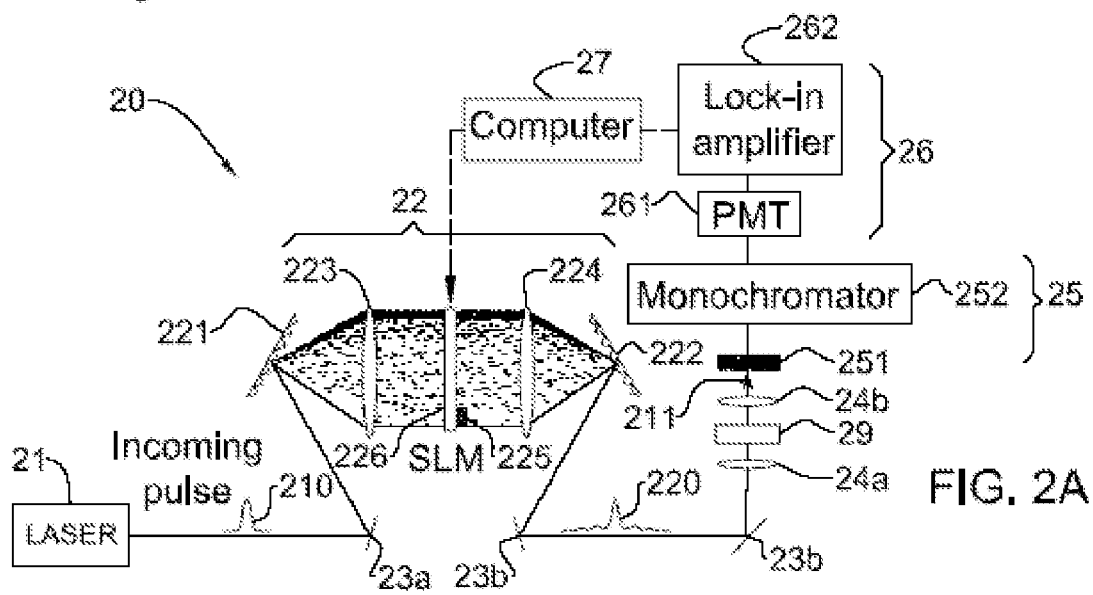
FIG. 2A illustrates a schematic view of a single-pulse CARS spectrometer system, according to one embodiment of the invention.

Referring to FIG. 2A, there is schematically illustrated a CARS measurement system (spectrometer) 20 according to one embodiment of the present invention associated with a sample holder 29 containing a medium under investigation. The CARS spectrometer system 20 includes a single laser 21 adapted for producing optical transform-limited driving pulses 210 wherein each such pulse carries a pump photon, a Stokes photon and a probe photon which are necessary for exciting the medium and inducing the CARS process therein, a programmable pulse shaper 22 operable for shaping the input transform limited driving pulse to produce a unitary optical excitation pulse carrying the pump, Stokes and probe photons, a detector unit 26 for collecting a CARS signal coming from the medium and generating data indicative thereof, and a light directing optics for directing the input pulses to the medium and directing the CARS signal to the detector.

The laser 21 can be any laser capable to generate transform limited pulses in a femtosecond (fs) time range. For example, the transform limited pulses can be in a range of about 5 fs to 100 fs and, preferably, between 10 fs and 20 fs). For example, a Ti:Sapphire laser oscillator capable of generating 20 fs full-width at half maximum (FWHM) transform limited pulses at 80 MHz, centered at 815 nm (corresponding to a bandwidth of about 75 nm or an energy span of 1100 $cm^{-1}$) can be employed for the purpose of the present invention. The programmable pulse shaper 22 is configured for shaping the input transform limited driving pulses by assigning a desired phase to each wavelength component of the transform limited optical pulse, preferably only in a predetermined wavelength range, i.e., outside that where the CARS signal is most likely to occur. The use of such a pulse shaper enables for coherently controlling the CARS process.

A sample of the input transform limited pulse 210 generated by the laser 21 is directed to the pulse shaper assembly 22 by a mirror 23a, and a shaped pulse 220 produced by the shaper assembly 22 is directed to the holder 29 by a further mirror 23b. Obviously, each of these single-mirror elements of the light directing optics may be replaced by one or more beam splitter and/or a set of mirrors, or any other known light deflecting means.

In the present example of FIG. 2A, the programmable pulse shaper 22 is a 4-f shaper that includes an input dispersive assembly 221, an output dispersive assembly 222; an input focusing element 223, an output focusing element 224; and a programmable Spatial Light Modulator (SLM) 226 located at the Fourier plane defined by the focusing elements 223 and 224. In the present example, also provided in the pulse shaper 22 is a blocking element 225.

For example, the dispersive assemblies 221, 222 can be thin ruled reflective gratings with 1200 lines/mm, and the focusing elements 223, 224 can be achromat lenses (e.g., with a focal length of 100 mm). Though the above embodiment uses ruled reflective gratings at the input and output of the pulse shaper to spatially disperse and recombine the various frequency components of the pulses, it should be pointed out that any other suitable dispersive elements can be used, e.g., transmission gratings, prisms, or combinations thereof. Furthermore, the function of the focusing elements 223, 224 in defining the system Fourier plane (focal plane) at which the SLM 226 is located, can be fulfilled by any other element having positive focusing power, e.g., a concave mirror.

The blocking element 225 is, for example, a plate arranged for blocking at the Fourier plane wavelengths shorter than a predetermined wavelength (e.g., 780 nm) in the range of a CARS signal, as they can spectrally overlap an output CARS signal 211. In the present example of FIG. 2A, the blocking element 225 is arranged between the SLM 226 and the output focusing element 224. However, as can be appreciated by a person skilled in the art, the blocking element 225 can be arranged either upstream or downstream of the SLM 226. Furthermore, the function of blocking element 225 can be fulfilled by any sharp-edge long-pass filter, e.g., a dielectric filter.

The programmable SLM 226 may be a liquid crystal based SLM of the type described by A. M. Weiner in the article published in Rev. Sci. Inst., 2000, V. 71, P. 1929. This SLM includes an SLM pixel array having 128 pixels at its Fourier plane. The spectral resolution, determined by the spot size at the Fourier plane, can be better than 0.5 nm (equivalent to about 8 $cm^{-1}$).

The operation of the 4-f pulse shaper 22 is as follows. The input dispersive element 221 operates to spatially separate the frequency components of the input transform limited pulse. The input focusing element 223 focuses each of these frequency components to its specific position at the focal plane, where the SLM 226 is located. The blocking element 225 blocks at the Fourier plane wavelengths shorter than the predetermined wavelength. The SLM 226 is operative as an updateable filter for spectral manipulation of the incoming pulses, and allows the independent control of the phase and amplitude of each of the light components passing through 128 pixels, thereby modifying the pulse shape and temporal profile according to the desired pulse properties. For example, the width of each pixel is 97 μm, the inter-pixel gap is 3 μm, while the spot size at the focal plane is about 80 μm. The output focusing element 224 and output dispersive element 222 then recombine each of the separate frequency components to produce a shaped pulse 220.

Thus, the programmable pulse shaper 22 of FIG. 2A is operable by a suitable control unit 27 for separating between different frequency components of the input pulse, blocking the predetermined frequencies (higher frequencies, which can overlap the CARS signal); and assigning the desired phase to each frequency component of the remaining (non-blocked) portion of the input pulse by using any desired spectral phase function.

The CARS spectrometer system 20 may utilize an open loop control, in which the applied spectral phase function is derived theoretically for each experiment, or may utilize a closed feedback loop for determining the applied spectral phase function.

The shaped pulse 220 produced by the pulse shaper 22 carries a pump photon, a Stokes photon and a probe photon (which are necessary for exciting the medium and inducing the CARS process therein) and is therefore also referred to as "the unitary optical excitation pulse".

The unitary optical excitation pulse 220 reflected from the mirror 23b is focused by a focusing assembly 24a onto the medium under investigation for exciting thereof and inducing a CARS process. In the present example, the focusing assembly 24a includes an objective lens arrangement having an NA=0.2 numerical aperture.

The light directing optics further includes a lens assembly 24b accommodated for collection of the output CARS signal of the medium. This lens assembly 24b, preferably, has numerical aperture similar or larger than that of the lens 24a. It should be noted that the focusing assembly 24a can also serve as a collecting optics in a back-scattered mode.

Further provided in the CARS spectrometer system 20 is a filtering assembly 25 operable for filtering the CARS signal obtained from the medium. In the present example, the filtering assembly 25 includes a spectral filter 251 (e.g., a bandpass or short-pass filter), and preferably includes a computer-controlled monochromator 252 or a spectrograph (not shown). An example of the filter 251 includes, but is not limited to, a 40 nm FWHM bandpass filter centered at 750 nm, while an example of the computer-controlled monochromator 252 includes, but is not limited to, a computer-controlled monochromator with a spectral resolution of 0.5 nm (equivalent to about 8 $cm^{-1}$ at 750 nm).

The filtered output of the filtering assembly 25 is collected by the detector unit 26, which includes a detector 261 of the kind receiving a light signal and generating an electrical output indicative thereof, and may also include a lock-in amplifier 262 operable by the control unit (computer) 27.

It should be appreciated that the construction and operation of the filter 251, monochromator 252, detector 261 and a lock-in amplifier 262 as well as the elements of the light directing optics, are known per se, and therefore need not be specifically described.

It should be noted that the measurable Raman energy range of the system 20 can, for example, be about 300 cm$^{-1}$-900 cm$^{-1}$, that is typical of carbon-halogen bond stretching. The lower limit of the measurable energy range is determined by the need to filter out the excitation pulse, while the upper limit is dictated by the excitation pulse bandwidth. Since the technique does not require an electronic resonance with the driving input field, it can be implemented with any broadband optic source 21. The measurable Raman energy range of the system 20 can be extended to the fingerprint region (900 cm$^{-1}$-1500 cm$^{-1}$) by using pulses of duration 10 fs-20 fs, available in the state-of-the-art commercially available lasers.

Figure 2B:
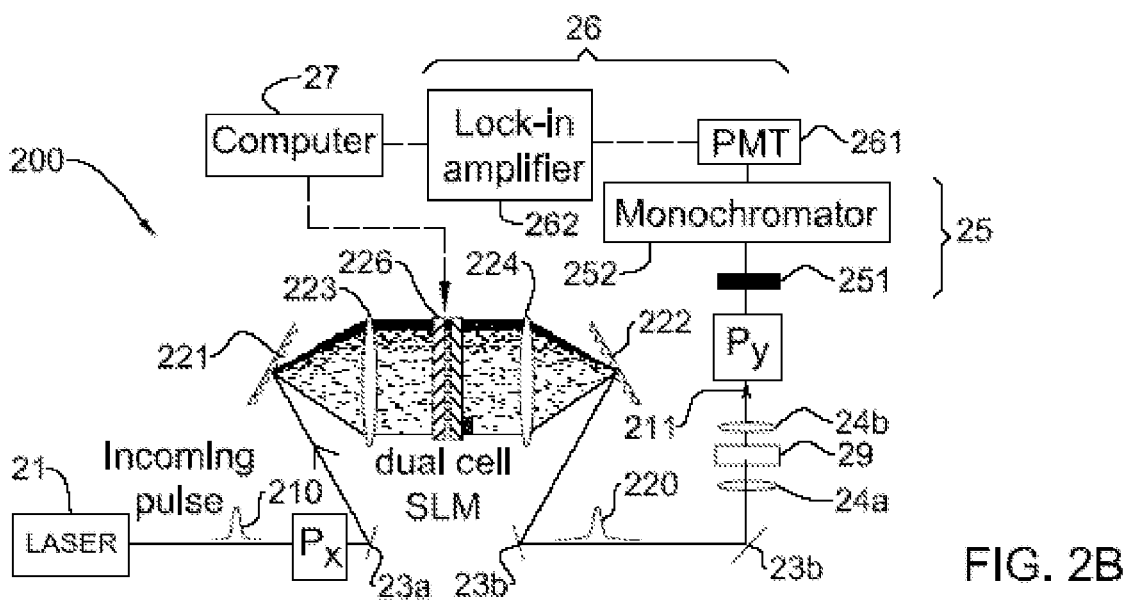
FIG. 2B illustrates a schematic view of a single-pulse CARS spectrometer system, according to another embodiment of the invention.

Referring to FIG. 2B, a schematic view of a CARS spectrometer system 200 according to another embodiment of the present invention is schematically illustrated. The CARS spectrometer system 200, distinguishes from the CARS system 20 shown in FIG. 2A in that its shaper assembly additionally to the phase modulator or as an alternative thereto comprises a polarization control assembly including a frequency-selective filter, such as grating 221, and a 90 degree polarization rotator accommodated in the optical path of the frequency components emerging from the filter and operable for applying a 90 degree polarization rotation to the predetermined frequency range of the input transform limited laser pulse, and comprises a crossed polarizer unit P$_y$ accommodated in the optical path of a signal propagating from the medium to the detector for extraction of the cross-polarized CARS signal.

In the present example of FIG. 2B, the polarization rotator is constituted by an SLM arrangement 226, but it should be understood that any other suitable means can be used (e.g., a half-wavelength assembly). Additionally, in the example of FIG. 2B, the polarization control assembly also includes a polarizer P$_x$ accommodated in the optical path of the transform limited laser pulse propagating towards the shaper assembly. It should however be understood that the provision of this input polarizer P$_x$ is optional, and can be eliminated by using a laser source producing linearly polarized light. In the example of FIG. 2B, the SLM unit can be operable for performing both the phase shaping and polarization rotation of the frequency components of the transform limited pulse. Generally, the phase assembly may comprise only a polarization rotator of any known suitable type. The SLM assembly suitable to be used in the system of the present invention may, for example, be of the type described by T. Brixner et al. in the articles published in Opt. Lett., 2001, V. 26, P. 557 and Appl. Phys., 2002, V. B74, P. S133. Such a programmable liquid crystal SLM 226 includes two SLM liquid crystal pixel arrays (dual cell SLM) whose preferential axes are at right angles to each other and are rotated by ±45° relative to the polarization of the input laser pulse (denoted as the x direction). Any difference in the applied retardance between the two arrays results in modification of the input pulse polarization. In this technique, the SLM can act as both a controlled spectral phase mask and as a controlled waveplate.

Thus, in this specific example, the programmable pulse shaper, in operates for both assigning the desired phase to each frequency component of the driving laser pulse, and a polarization control of the pulse. In particular, the polarization control can be used to break the ultrashort input pulse 210 into a broadband pump and a narrow-band probe with orthogonal polarizations.

The nonlinear polarization producing the CARS signal driven by an electric field of the excitation pulse whose spectrum is E(ω) can be approximated for nonresonant transitions, by using time dependent perturbation theory, as (for more details see, for example, Oron et al., Phys. Rev. Lett., 2002, V. 88, P. 63004):

$$P_{nr}^{(3)} \propto \int_0^\infty d\Omega E(\omega - \Omega) A(\Omega), \quad (1)$$

where $$A(\Omega) = \int_0^\infty d\omega' E^*(\omega' - \Omega) E(\omega')$$

is the probability amplitude to populate a vibrational level with energy $\hbar\Omega$ (henceforth, the population amplitude), while E(ω−Ω) represents the probe field.

Similarly, the nonlinear polarization for a singly resonant Raman transition through an intermediate level |i⟩ at an energy of $\hbar\Omega_R$ and a bandwidth Γ can be approximated by $$P_r^{(3)} \propto \int_0^\infty d\Omega \frac{E(\omega - \Omega)}{(\Omega_R - \Omega) + i\Gamma} A(\Omega). \quad (2)$$

The CARS process can be controlled by controlling the population amplitude A(Ω). The control of A(Ω) is accomplished by controlling the spectral phase of the single broadband excitation pulse. Such a phase-only pulse shaping of the pulse merely means multiplication of the electric field E(ω) (that includes pump, Stockes and probe photons) by a phase function exp(iΦ(ω)).

The population of a vibrational level at energy $\hbar\Omega_R$ is proportional to $$|A(\Omega)|^2 = \left| \int d\omega E(\omega) E^*(\omega - \Omega_R) \right|^2, \quad (3)$$

where E=|E(ω)|exp(iΦ(ω)) is the complex spectral amplitudes of the applied field. Each level is thus excited by all frequency pairs separated by Ω$_R$. The interference between the multiple paths leading to the population of the level Ω$_R$ is determined by the relative phase of each contribution Φ(ω)−Φ(ω−Ω$_R$). Thus, constructive interference is achieved when Φ(ω)=Φ(ω−Ω$_R$) for all frequency components of the excitation pulse. Therefore, if the excitation pulse is a transform-limited pulse (all frequency components having the same phase), then the constructive interference holds for all values of Ω$_R$, thus spectral resolution is lost.

Figure 3A:
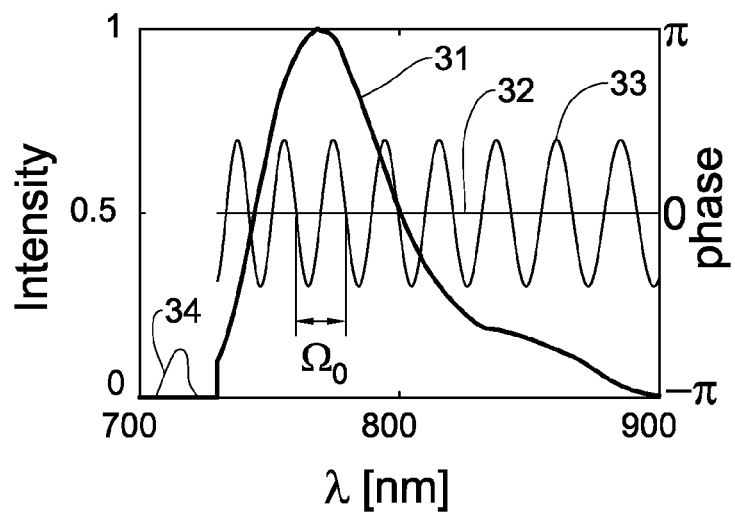
FIG. 3A to FIG. 3C illustrate effect of a modulated spectral phase function on the temporal shape of the pulse and on the population amplitude.
Figure 3B:
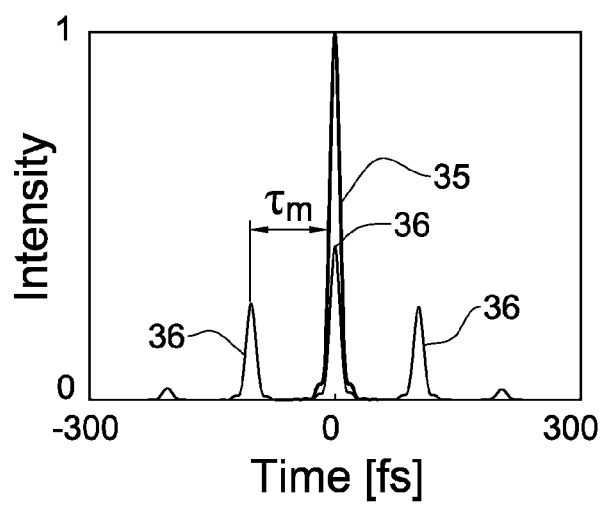
Figure 3C:
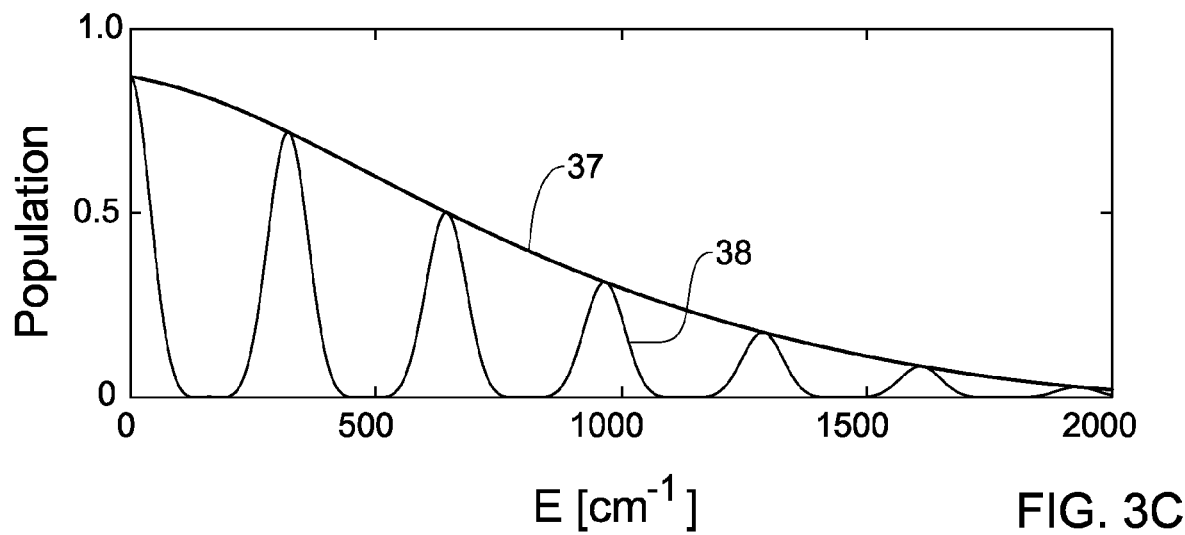

According to one example of the phase control, that has been first described by the inventors in an article entitled "*Single-pulse coherently-controlled nonlinear Raman spectroscopy and microscopy*" published in Nature, V. 418, PP. 512-514 (August 2002), the spectral phase of the excitation pulse is modulated periodically with a period Ω$_0$. In such a case, the constructive interference can be induced for all energy levels only for $\Omega_R = N\Omega_0$ (where N is an integer). FIGS. 3A-3C illustrate an effect of a modulated spectral phase function on the temporal shape of the pulse and on the population amplitude, according to this specific example of the phase control.

FIG. 3A shows an example of an input pulse spectral intensity 31, a spectral phase 32 of the transform limited pulse, and a modulated spectral phase 33 of the shaped pulse (unitary excitation pulse). Also shown is a typical spectral region where the CARS signal can be measured. Thus, in order to avoid the spectral overlap between the input pulse and a CARS signal, the power spectrum of the input pulse is blocked at 730 nm. (Note that the spectral intensity of the CARS signal is identified by a reference numeral 34).

FIG. 3B shows in time domain a temporal intensity of transform limited pulse 35 corresponding to the uniform phase (32 in FIG. 3A), and a modulated phase shaped pulse 36 corresponding to the modulated phase (33 in FIG. 3A). As can be understood from FIG. 3B, a periodic spectral phase is equivalent to splitting the pulse in time domain to several equally spaced pulses, each delayed by $\tau_0 = 2\pi/\Omega_0$. This pulse train is capable of resonantly exciting only vibrations with a period $T = \tau_0/N$.

FIG. 3C shows a calculated population amplitude $A(\Omega)$ for the transform limited pulse 37 and for the pulse having the modulated phase 38. As can be seen in FIG. 3C, for the case of the transform limited pulse, the population amplitude decays monotonically versus the vibration energy. On the other hand, for the case of a modulated phase function, an oscillation appears where the peak of each oscillation reaches the transform limited result.

The resonant and nonresonant processes described above have different spectral responses, which result from the different weights that multiply the population amplitude in Eq. (2) and Eq. (3), as determined by the resonance levels.

According to Eq. (2), the resonant CARS process can be expressed as $$P_r^{(3)} \approx C\left[i\pi E(\omega - \Omega_R)A(\Omega_R) + \varsigma \int_0^\infty d\Omega \frac{\Omega - \Omega_R}{(\Omega - \Omega_R)^2 - \Gamma_R^2} E(\omega - \Omega)A(\Omega)\right] \quad (4)$$

where $\varsigma$ is the principal value of Cauchy. The first term in Eq. (4) corresponds to the "on-resonant" contribution, while the second term corresponds to integration over the contribution of the "off-resonant" spectral components. The resonant signal thus has a narrow response around $\Omega = \Omega_R$.

The weight function of the integrand of the second term inverts its sign around the resonance, therefore the total contribution of the integral depends on the symmetry of $E(\omega-\Omega)A(\Omega)$ around $\Omega=\Omega_R$. In the transform limited case, both $A(\Omega)$ and $E(\omega-\Omega)$ are nearly symmetric for all values of $\Omega$. Therefore, the off-resonant term is negligible. The polarization spectrum can be approximated in this case by $$P_r^{(3)} \sim i\pi CE(\omega-\Omega_R)A(\Omega_R) \quad (5)$$

which is a replica of the pulse spectrum shifted by $\Omega_R$. Spectral phase manipulation will change the symmetry of $E(\omega-\Omega)A(\Omega)$ for different values $\omega$, and will therefore induce variations of the polarization spectrum.

However, when the modulation frequency significantly exceeds $2\pi/\Delta\omega$ (here, $\Delta\omega$ is the pulse spectral bandwidth), the total signal intensity averages out and is proportional to $|A(\Omega_R)|^2$.

By the same token, the measured nonresonant intensity averages out to become proportional to $$\left|\int \frac{d\Omega}{\Omega} A(\Omega)\right|^2.$$

The total measured signal is the interference of the signals generated by the two different processes. In the common case where the nonresonant background is considerably larger than the resonant signal, the resonant signal is measured by a "heterodyne detection" with it, to yield $$|P^{(3)}(\omega)|^2 = |P_r^{(3)}(\omega) + P_{nr}^{(3)}(\omega)|^2 \sim P_r^{(3)}(\omega)|^2 + 2Re[P_r^{(3)}(\omega)P_{nr}^{(3)}(\omega)^*]. \quad (6)$$

By exploiting the different spectral response of the resonant and nonresonant components, it is possible to significantly reduce the nonresonant background while maintaining the resonant signal. Following the above derivation, it can be clear to a person versed in the art that properly choosing the periodicity of the phase function, the population and thus the resonant CARS signal is reconstructed to nearly the value achieved by a transform limited pulse.

Thus, it was shown above that the coherent control of the CARS process via manipulation of the vibrational level population amplitude $A(\Omega)$ can be accomplished by applying periodic spectral phase function (e.g., sinusoidal function) producing periodical modulation of the spectral phase of the excitation pulse.

Figures 4A, 4B, 4C:
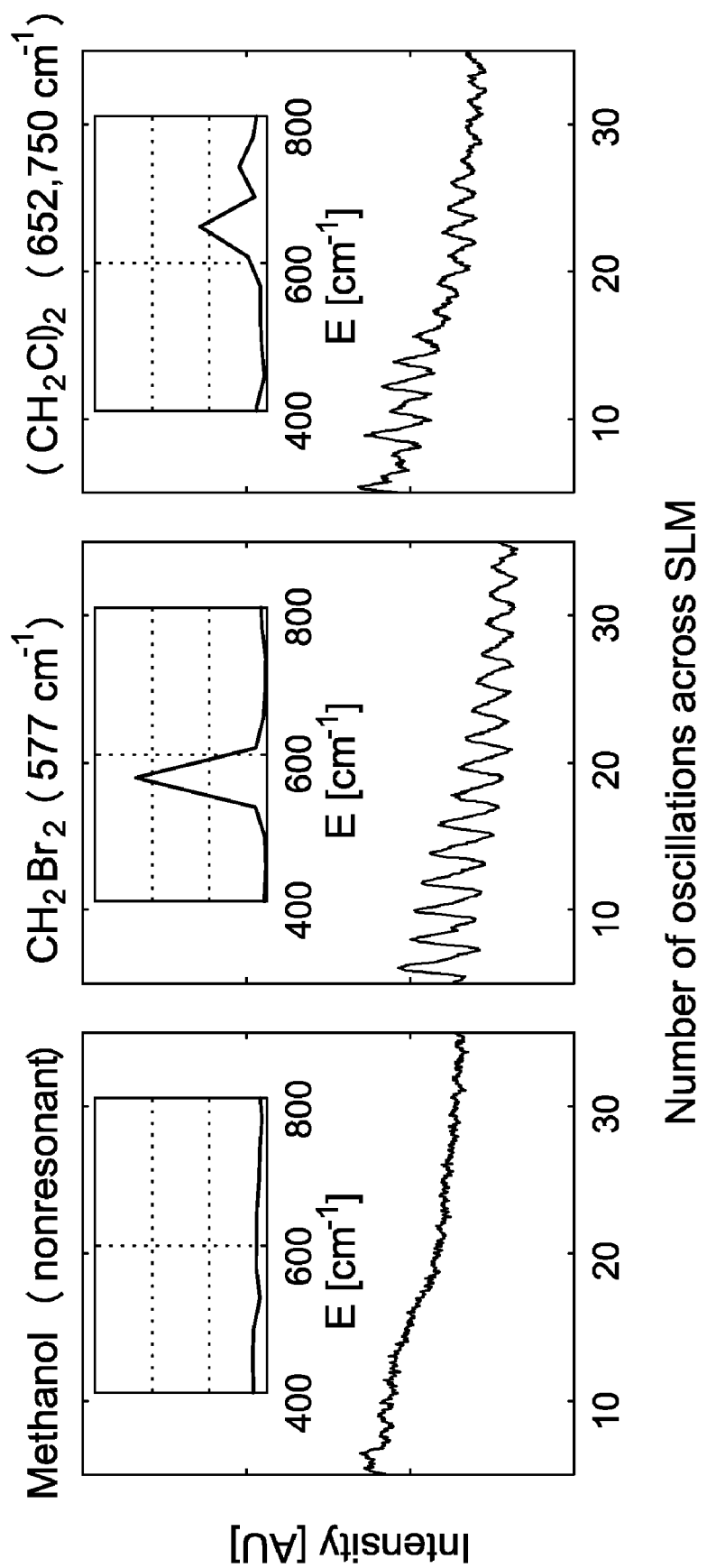
FIG. 4A to FIG. 4C illustrate examples of measurements of the Raman spectra obtained by varying the phase function periodicity.

Referring to FIGS. 4A-4C, measurements of the Raman spectrum are exemplified. The Raman spectrum has been obtained by monitoring the total CARS signal, while varying the phase function periodicity. According to this examples, a simple periodic spectral phase function $\Phi(\omega) = 1.25 \cos(C\omega)$ (wherein C is a constant) has been applied to the input transform limited pulse for its shaping. Presented in FIGS. 4A-4C are the intensities of the CARS signal versus the number of periods of the sinusoidal phase across the spatial light modulator (SLM). The insets show the Raman spectrum, derived by Fourier transformation of the corresponding measured intensity signals.

More specifically, FIG. 4A illustrates single-pulse CARS spectroscopy of methanol molecules in the liquid phase. As can be seen for methanol, which has no Raman resonance levels at the measured frequency range, only a monotonic decrease of the nonresonant signal is observed as the number of oscillation periods is increased.

FIG. 4B illustrates single-pulse CARS spectroscopy of $CH_2Br_2$ molecules in the liquid phase. As can be seen, for $CH_2Br_2$, which has a single resonance at $\Omega_R = 577$ cm$^{-1}$, the Raman signal oscillates periodically, whenever the modulation period is an integer fraction of $\Omega_R$. The Fourier transform operation retrieves the single Raman resonant level with a resolution that is inversely proportional to the number of modulation periods.

FIG. 4C illustrates single-pulse CARS spectroscopy of $(CH_2Cl)_2$ molecules in the liquid phase. As can be seen, for the material with two resonant levels, such as $(CH_2Cl)_2$, two resonant peaks (at 652 cm$^{-1}$ and 750 cm$^{-1}$) are observed in the Raman spectrum.

The spectral resolution of the Fourier transform operation is better than the pulse bandwidth by a factor of 40 (i.e., about 30 cm$^{-1}$). It is limited by the maximal number of phase modulation periods on the spatial light modulator (SLM), technically determined by the number of pixels on the SLM.

Thus, spectral resolution can be optimized by employing a simple sinusoidal phase function. Breaking the single pulse into a longer train, than used in the above example, containing a larger number of pulses can further reduce the nonresonant background, which depends directly on the pulse peak intensity. This is achieved by adding higher harmonics orders to the applied phase functions. This phase function can be expressed as a summation of the different harmonics orders as $$\Phi(\omega) = \sum_n A_n \cos(C_n \omega),$$

where $A_n$ are the different harmonic order coefficients.

Figures 5A, 5B:
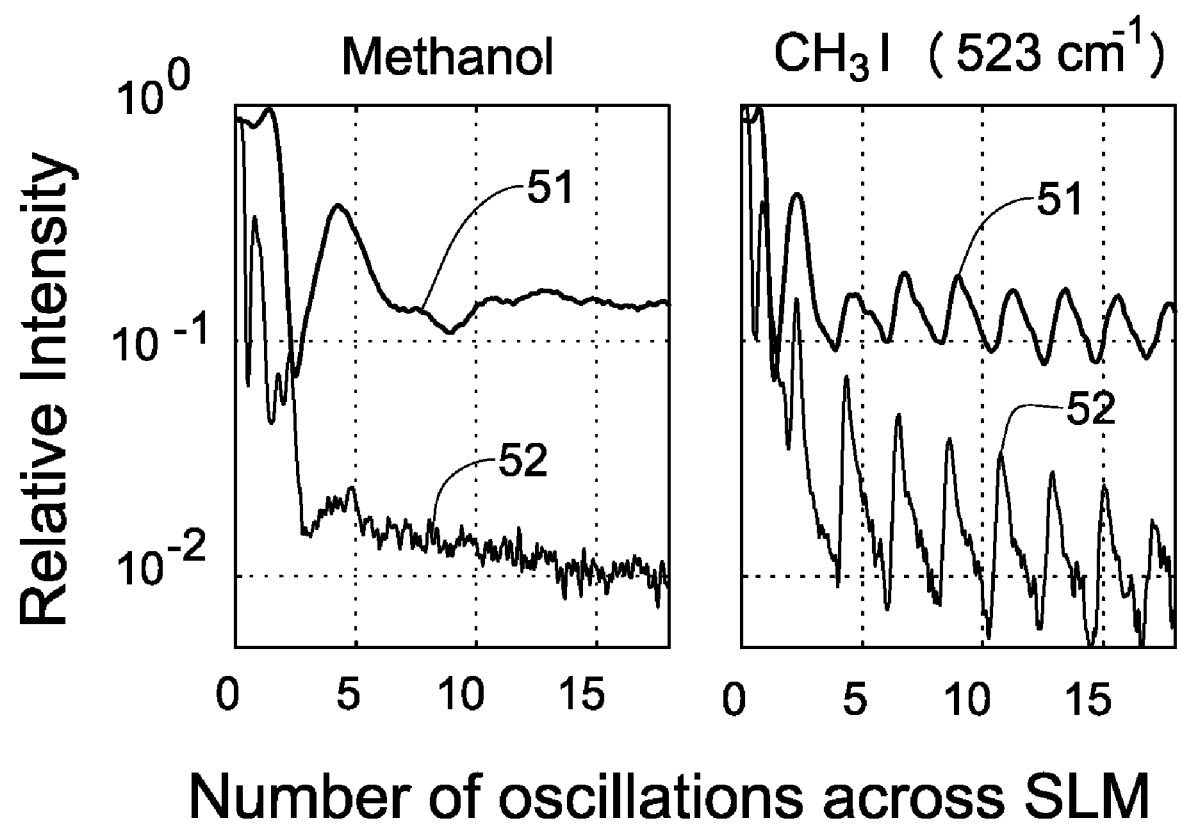
FIG. 5A to FIG. 5B illustrate the nonresonant background suppression by using periodic spectral function with additional harmonics.

Referring to FIGS. 5A-5B, a demonstration of the nonresonant background suppression by using periodic spectral functions with additional harmonics is illustrated for methanol (nonresonant component only) and CH$_3$I (a single resonance at 523 cm$^{-1}$), respectively. The CARS signal of relative intensity is shown versus the number of phase oscillation periods across the spatial light modulator for both a sinusoidal phase function $\Phi(\omega)=1.25 \cos(C\omega)$ (curve 51) and a phase function $\Phi(\omega)=1.4 \cos(C\omega)-1.4 \cos(2C\omega)$ which contains an additional harmonic component (curve 52). The CARS signal is plotted relative to that obtained by a transform-limited pulse (0 phase function oscillations). It should be noted that to achieve adequate suppression of the nonresonant background at least several oscillation periods of the phase function across the pulse spectrum are necessary.

FIG. 5A shows how the use of a phase function containing only one additional harmonic allows for attenuating the nonresonant background by nearly two orders of magnitude.

FIG. 5B shows that the use of a phase function containing two components attenuates significantly the nonresonant background, while the resonant component is almost completely restored. The achieved contrast between the resonant signal and the nonresonant background is thus greatly improved.

According to another example of the phase control, the spectral phase of the excitation pulse can be controlled by applying to the excitation pulse a narrow-band phase gate near its short wavelength (high-energy) end. In other words, a narrow-band feature is applied to the pulse for inducing sharp changes in the phase of the factor $E(\omega-\Omega)$ in Eqs. (1) and (2). Preferably, but not necessarily, the phase of the phase gate spectral function can be shifted by $\pi$ at $\omega-\Omega$. Such spectral phase function hereinafter will be referred to as a $\pi$ phase gate. For example, a bandwidth of the $\pi$ phase gate can be in the range of about 0.5 nm to 3 nm (i.e., 5-30 cm$^{-1}$). Preferably, the $\pi$ phase gate is spectrally located in the vicinity of a short wavelength end of the excitation pulse.

In this scheme, a narrow spectral band in the excitation pulse is phase shifted, serving as an effective probe, and the Raman spectrum is extracted from the interference pattern of the resonant signal with the nonresonant background.

Figure 6A:
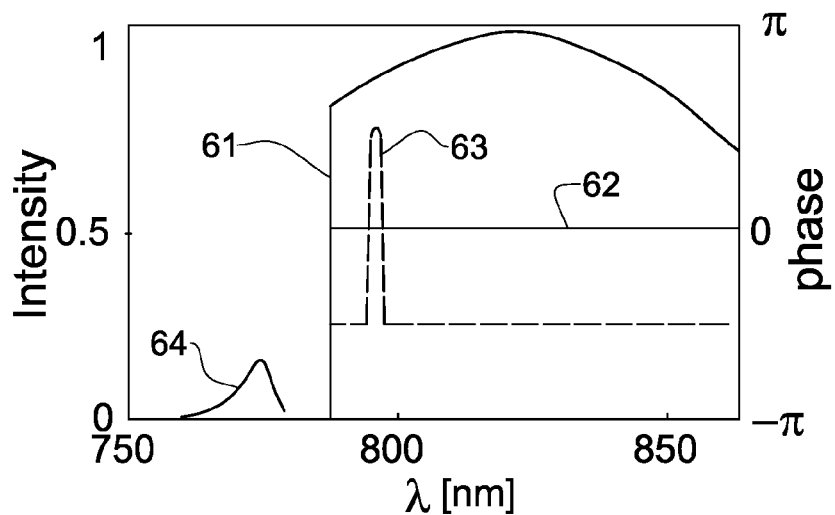
FIG. 6A to FIG. 6C illustrate effect of a π phase gate phase function on the temporal shape of the pulse and on the population amplitude.
Figure 6B:
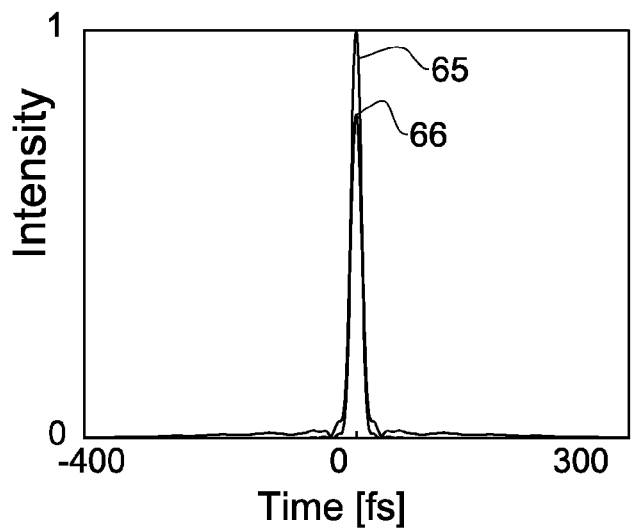
Figure 6C:
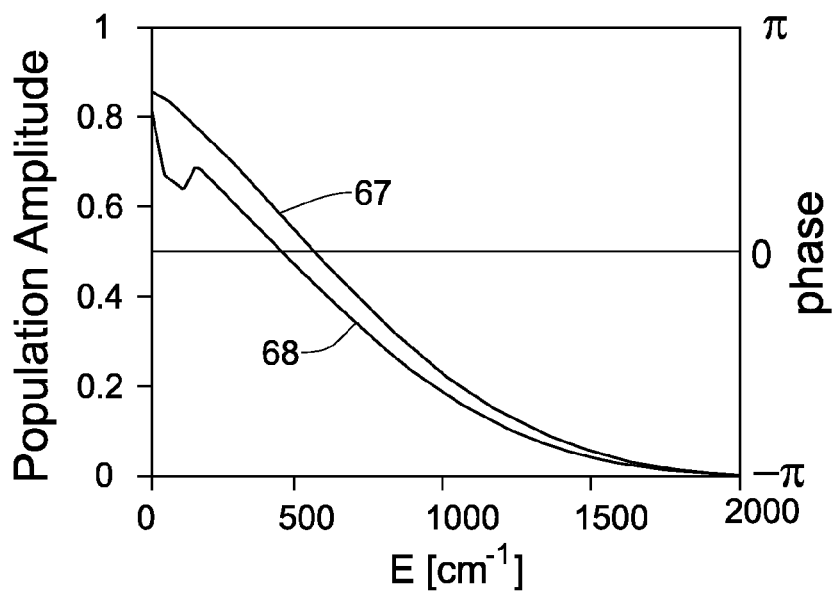

Referring to FIGS. 6A-6C, there is illustrated an effect of a $\pi$ phase gate on the temporal shape of the pulse and on the population amplitude, according to this specific example of the phase control.

FIG. 6A shows an example of the excitation pulse spectral intensity 61, a spectral phase 62 of the transform limited (unshaped) pulse, and a $\pi$ phase-gate 63 of the shaped pulse. In this example, the $\pi$ phase-gate 63 has the bandwidth of about 1.5 nm centered at 790 nm. Also shown is a typical spectral region where the CARS signal can be measured. Thus, in order to avoid the spectral overlap between the input pulse and a CARS signal the power spectrum of the input pulse is blocked at about 780 nm. Note that the spectral intensity of the CARS signal is identified by a reference numeral 64.

FIG. 6B shows in time domain a temporal intensity (temporal envelope) of a transform limited pulse 65 and a temporal intensity of a $\pi$ phase-gate shaped pulse 66. As can be seen, the narrow $\pi$ phase gate hardly effect the form of the pulse, merely reducing the peak intensity by about 15%.

FIG. 6C shows a calculated population amplitude $A(\Omega)$ for the transform limited pulse 67 and for the pulse having the modulated phase 68. As can be seen in FIG. 6C, for the case of the transform limited pulse, the population amplitude decays monotonically versus the vibration energy. The changes due to the phase gate slightly modify the population amplitude $A(\Omega)$. This modification depends on the width of the phase gate. Thus, the population amplitude $A(\Omega)$ is hardly modified for a narrow gate, since the energy content in a narrow spectral band part is negligible compared with the entire pulse energy.

The resonant signal from a level $\Omega_R$ at any given frequency $\omega$ is centered at $\omega-\Omega_R$, due to a rather narrow band probe. In contrast, the nonresonant background signal is a coherent sum contributed by a large portion of the pulse bandwidth. Thus, phase changes over a narrow spectral band, while dramatically affecting the phase of the resonant signal, hardly modify the phase of the nonresonant signal. The relative phase between the nonresonant background signal and the resonant signal should therefore vary rapidly, inducing either constructive or destructive interference at the phase gate edges. Measuring the total CARS spectrum, the interference pattern between the resonant signal and the nonresonant background can be interpreted to reveal the vibrational energy level diagram.

The effect of the phase control by using an excitation phase with a narrow-band phase gate is demonstrated in the numerical simulation results shown in FIGS. 7A-7D.

Figure 7A:
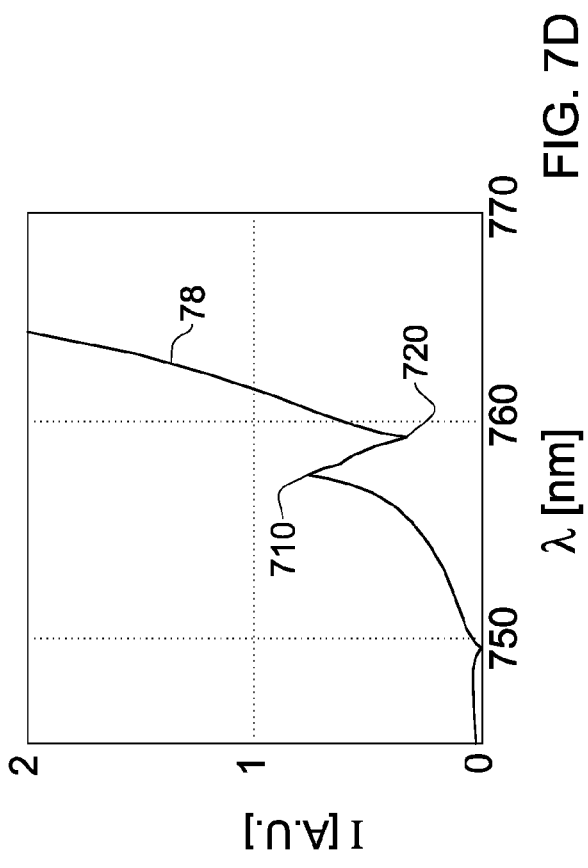
FIG. 7A to FIG. 7D are examples of a numerical simulation illustrating the effect of the phase control by using an excitation phase with a narrow-band phase gate.
Figure 7B:
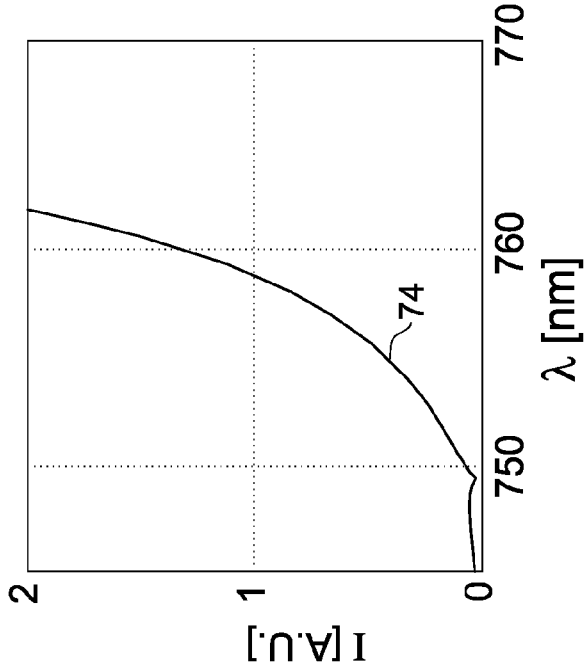

FIG. 7A shows a calculated CARS electric field as a function of frequency (spectrum) of both the resonant contribution 71 and the nonresonant contribution 72 along with the relative phase 73 between them for a transform limited pulse illuminating of iodomethane (resonant at 523 cm$^{-1}$). FIG. 7B shows the calculated resulting CARS spectrum 74 for the illuminating of iodomethane with a transform limited pulse.

As can be seen, the nonresonant background spectrum 72 monotonically decreases towards higher energies (short wavelengths), while the resonant signal 71 resembles the excitation pulse spectrum, shifted by the Raman level energy. The relative phase 73 between the two is nearly constant at about $\pi/2$, rising to about $\pi$ below 749 nm.

Figure 7C:
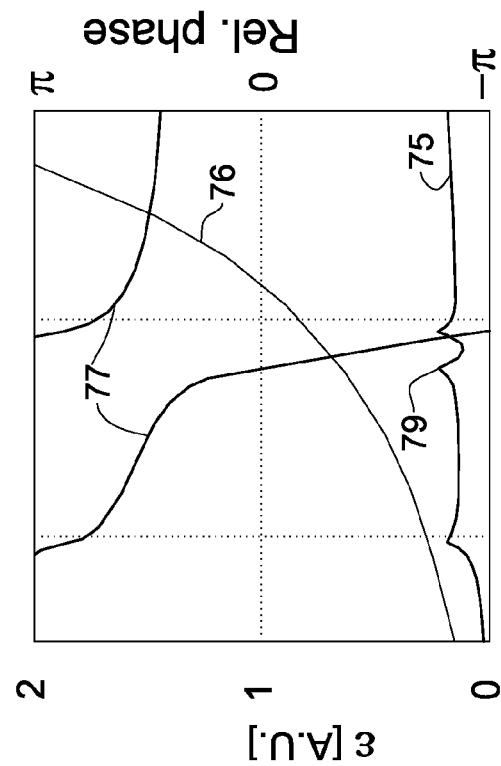
Figure 7D:
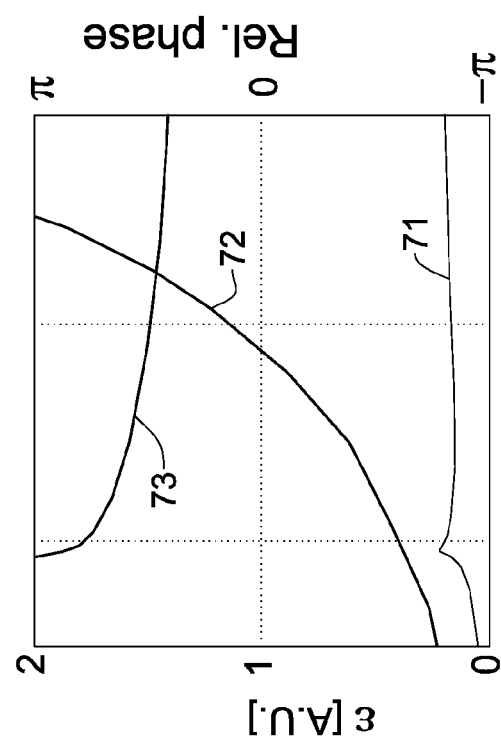

FIG. 7C shows a calculated CARS spectrum of both the resonant contribution 75 and the nonresonant contribution 76 along with the relative phase 77 between them for the illuminating of iodomethane by a $\pi$ phase gate shaped pulse. FIG. 7D shows the calculated resulting CARS spectrum 78 for the transform limited pulse illuminating of iodomethane. Three effects can be seen in FIG. 7C. First, there is some reduction of the nonresonant background component. Second, the relative phase between the resonant component and the nonresonant background component varies between 0 (constructive interference) at the high-energy (short wavelength) side of the gate, and $\pi$ (destructive interference) at the low energy (long wavelength) side. Third, two new peaks 79 appear in the resonant spectrum 75, at both ends of the phase gate. The peaks 79 are due to a transient enhancement effect demonstrated by Oron et al. previously in conventional multi-beam CARS and described in Phys. Rev. Lett., 2002, V. 88, P. 63004.

As can be seen in FIG. 7D, the net result is a sharp peak 710, followed by a deep dip 720 in the total CARS signal 78. It should be noted that this peak-dip feature determines the energy of the vibrational level with an accuracy of the phase gate width. For example, the phase gate can be defined by three pixels on the SLM, corresponding, to about 25 cm$^{-1}$, that is about 40 times better than the excitation pulse width.

Figure 8A:
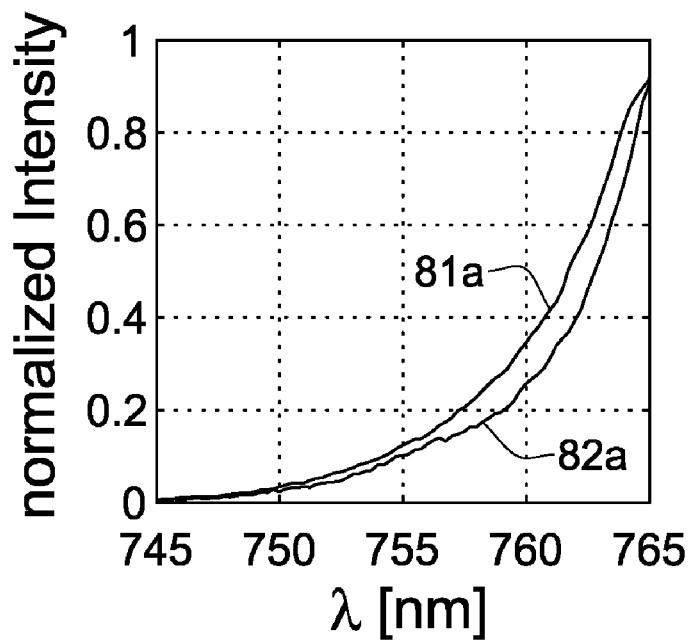
FIG. 8A and FIG. 8B illustrate measured normalized CARS spectra by using a transform limited pulse a phase gate shaped pulse for methanol and iodomethane, correspondingly.
Figure 8B:
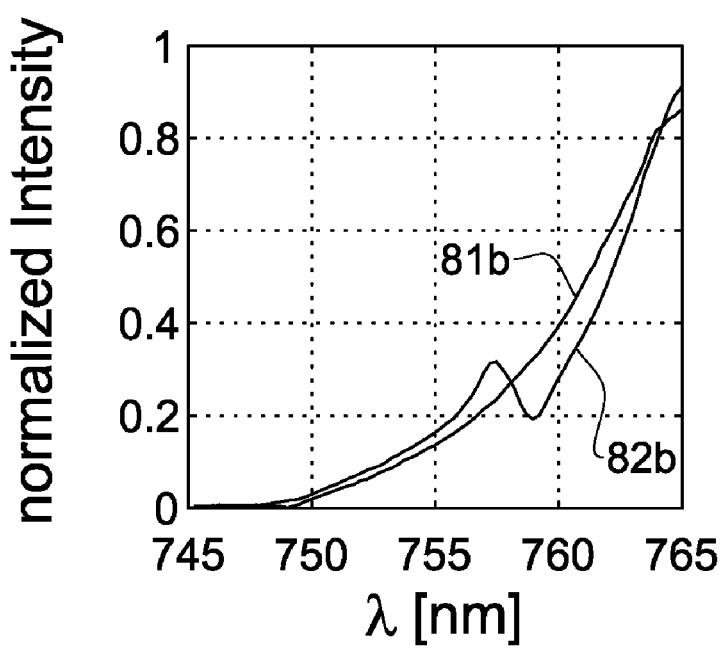

Referring to FIGS. 8A and 8B, there are illustrated measured normalized CARS spectra for the case of a transform limited pulse (curves 81a and 81b) and the case of a phase gate shaped pulse (curves 82a and 82b), respectively, for methanol (having nonresonant component only) and for iodomethane (having a resonant at 523 cm$^{-1}$). The peak-dip feature due to the resonant contribution at 523 cm$^{-1}$ can be seen in the iodomethane spectrum (FIG. 8B), while the normalized methanol spectrum (FIG. 8A) remains nearly unchanged.

The Raman level structure can be easily extracted from the measured spectrum by considering, for example, the normalized spectral intensity variation of the CARS signal $$f(\Omega) = -\frac{I(\omega_g + \Omega - \Delta/2) - I(\omega_g + \Omega + \Delta/2)}{\int_{\omega_g+\Omega-\Delta/2}^{\omega_g+\Omega+\Delta/2} I(\omega)d\omega} \tag{7}$$

where $\omega_g$ is the central frequency of the phase gate and $\Delta$ is the gate width. It should be understood that the normalization is required to compensate for the decrease in the nonresonant background towards higher energies.

Referring to FIGS. 9A-9D, plots of the normalized spectral intensity $f(\Omega)$ derived from the measured CARS spectra (curves 91, 92, 93 and 94) are given in for several materials, along with simulation predictions (curves 95, 96, 97 and 98) obtained by computer simulations.

Figure 9A:
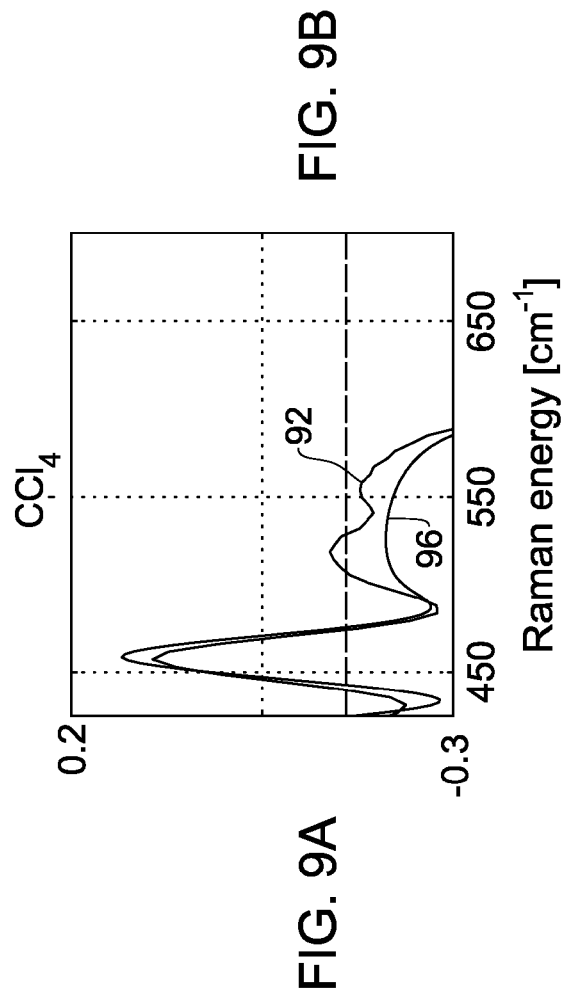
FIG. 9A to FIG. 9D illustrate the normalized spectral intensity derived from the measured CARS spectra along with those obtained by computer simulations for several materials.
Figure 9B:
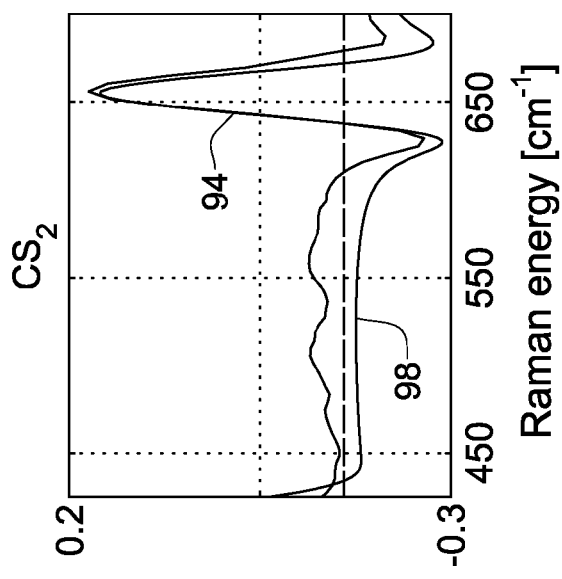
Figure 9C:
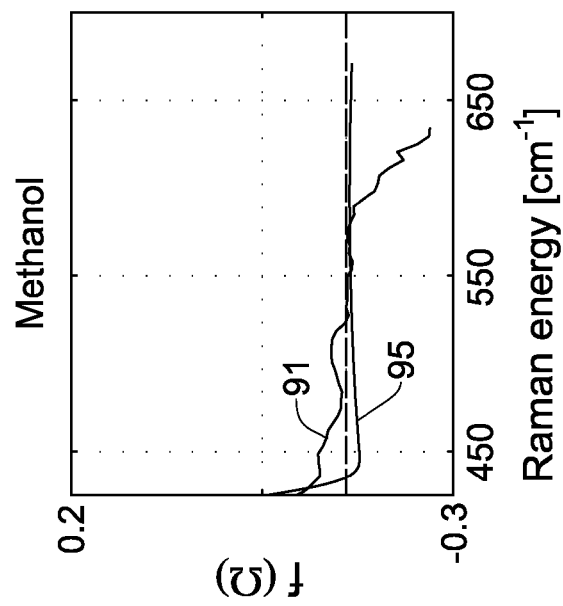
Figure 9D:
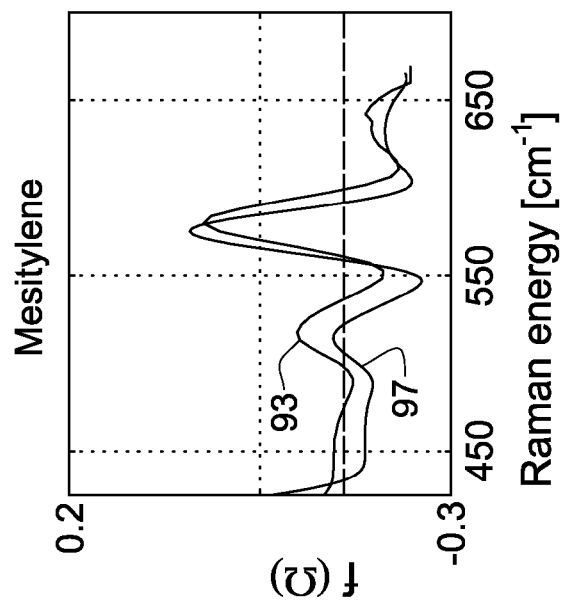
Figure 10A:
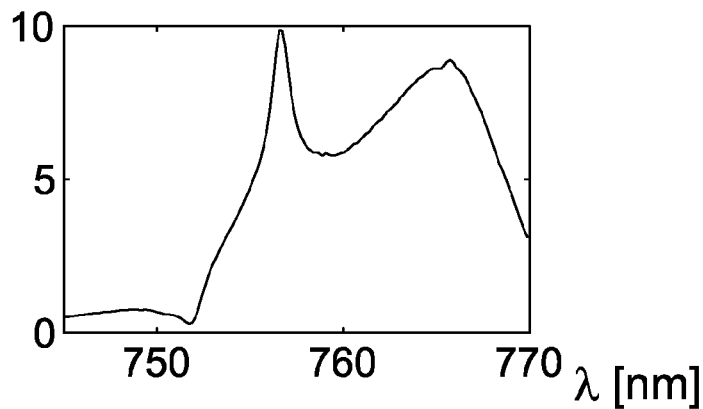
FIG. 10A to FIG. 10D illustrate CARS spectra from iodomethane obtained with polarization-only shaping and plotted for various probe bandwidths.
Figure 10B:
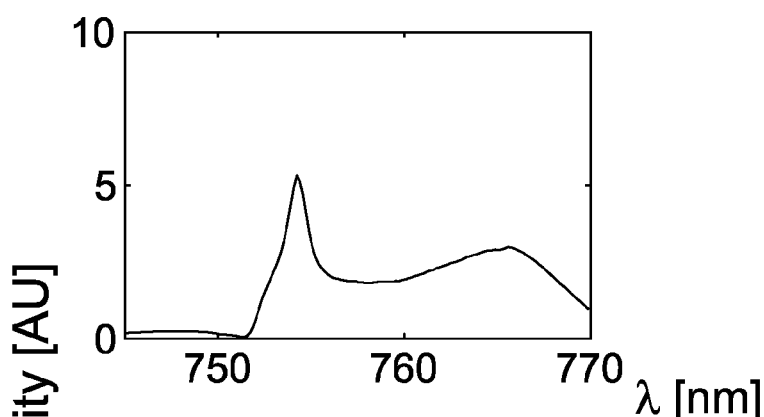
Figure 10C:
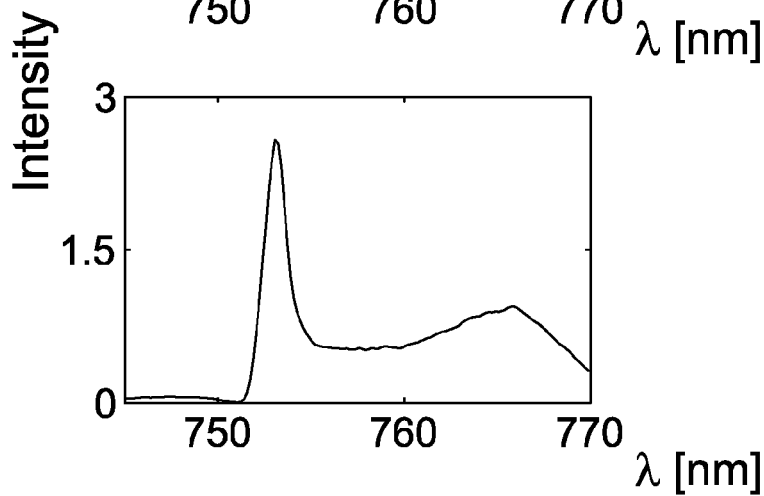
Figure 10D:
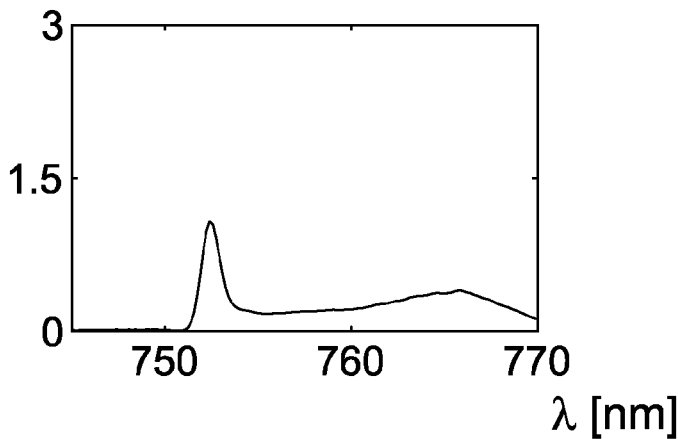

As can be seen in FIG. 9A, nearly flat line is observed for methanol, having no Raman level in this range. The 459 cm$^{-1}$ level of carbon tetrachloride is easily observed in FIG. 9B. For mesitylene (FIG. 9C), having two Raman levels at 515 cm$^{-1}$ and 575 cm$^{-1}$ two well-separated peaks can be seen. At the high-energy end, the 652 cm$^{-1}$ level of carbon disulfide is shown in FIG. 9D. It should be noted that the spectral resolution observed in these figures is of the order of about 30 cm$^{-1}$, (i.e., almost a factor of 40 better than the excitation pulse bandwidth). The resolution is determined by both the width of the phase gate (25 cm$^{-1}$) and the monochromator resolution (about 8 cm$^{-1}$). The minimal phase gate width is determined by both the pixellization of the SLM and by the spot size of the incident beam on it. In all the examples presented above the phase gate consisted of three pixels on the SLM.

It should be understood that for detection of a given Raman level, it is possible to control the relative intensity ratio between the resonant and the nonresonant components by varying the spectral location of the phase gate. This is due to the fact that the nonresonant background decreases towards higher energies. Additionally, a further control is possible by varying the phase gate width. Thus, a wider probe width can improve the resonant to nonresonant intensity ratio (while resulting in lower spectral resolution). In this case, even weak Raman levels can be observed by using this scheme.

The benefits of broadband excitation can be fully exploited when attempting to detect materials with several vibrational bands in the measured energy range. In this case, a spectral phase mask having multiple phase gates at appropriate locations can be used to generate a large coherent spectral feature in the CARS spectrum, due to the constructive interference of the resonant contributions from the various levels.

According to another embodiment of the invention, the CARS process is controlled by controlling the polarization of the excitation pulse. It should be appreciated that the polarization control can be carried out in addition to the shaping, i.e., correcting of the dispersion of the input pulse and assigning of the desired phase to each frequency component of the driving pulse.

In particular, the polarization control can be used to break the ultrashort input pulse into a broadband pump and a narrow-band probe with orthogonal polarizations.

The nonlinear polarization producing the CARS signal driven by an electric field whose spectrum is $E(\omega)$ can be approximated for nonresonant transitions:

$$P^{(3)}_{nr(j)} \propto \chi^{nr}_{jklm} \int_0^\infty d\Omega E_k(\omega - \Omega) A_{lm}(\Omega), \tag{8}$$

where $A_{lm}(\Omega) = \int_0^\infty d\omega' E_l^*(\omega'-\Omega)E_m(\omega')$ is the population amplitude and $\chi_{jklm}^{nr}$ is the third order susceptibility tensor.

In turn, for a singly resonant Raman transition through an intermediate level $|i\rangle$ at an energy of $\hbar\Omega_R$ and a bandwidth $\Gamma$ one can obtain:

$$P^{(3)}_{r(j)} \propto \chi^{nr}_{jklm} \int_0^\infty d\Omega \frac{E_k(\omega-\Omega)}{(\Omega_R - \Omega)+i\Gamma} A_{lm}(\Omega). \tag{9}$$

The two main differences between the resonant and nonresonant components are as follows. First, the resonant component has a narrow spectral response, centered at $\Omega=\Omega_R$, whereas the spectral response of the nonresonant component is broad. Second, the response of the resonant component inverts sign at about $\Omega=\Omega_R$, while the nonresonant response has a constant phase. It will be shown hereinbelow how these differences are used to reduce the nonresonant component while enhancing the resonant component.

One approach to single-pulse polarization controlled CARS would be to rotate by $\pi/2$ the polarization of the excitation pulse in a narrow band at its high energy end, from an x-plane to a y-plane, and to monitor the CARS signal in the y-plane. As a result, the monitored signal will effectively dependent only on $A_{xx}$ (as the polarization field), and on $E_y$ (as the probe). This is true for both the resonant and nonresonant terms.

As was mentioned above for the case of the coherent control by means of a phase gate, the ratio of the resonant signal to the nonresonant signal of the background as well as the spectral resolution can be improved when the probe pulse becomes longer. According to this embodiment of the invention, the duration of the probe pulse is determined by the spectral width of the polarization shifted band.

Referring to FIGS. 10A-10D, examples of the CARS spectra from iodomethane obtained with polarization-only shaping are plotted for various polarized probe spectral bandwidths. The total bandwidth of the polarized probe decreases as follows: 4.5 nm (for the example shown in FIG. 10A); 2.3 nm (for the example shown in FIG. 10B); 1.2 nm (for the example shown in FIG. 10C) and 0.6 nm (for the example shown in FIG. 10D). As the probe bandwidth is decreased from 4.5 nm (corresponding to 400 fs) to 0.6 nm (corresponding to 3 ps, the resonant component, due to its narrow spectral response, becomes narrower but maintains its strength. In contrast, the nonresonant background component, having a broad spectral response, becomes weaker but maintains its spectral shape. Since the two are coherent, they generate an interference pattern, interfering constructively at the low-energy end of the probe pulse, and destructively at its high-energy end. This interference pattern obscures the interpretation and calls for further reduction of the nonresonant background.

Further reduction of the nonresonant background is achieved by using both the polarization control and the phase control. It will be shown below that the combination of both the phase and the polarization controls can lead to nearly complete suppression of the nonresonant component, yielding background-free single-pulse multiplex CARS spectra with a high spectral resolution.

Figure 11:
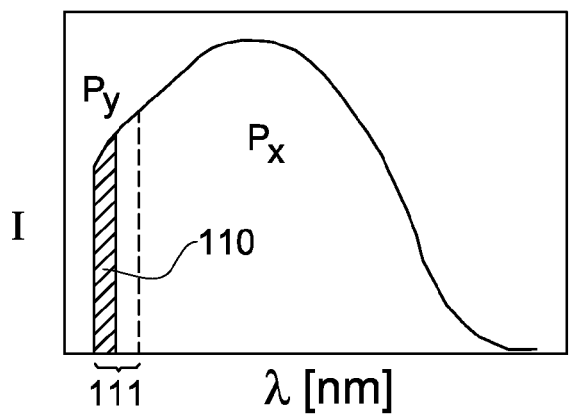
FIG. 11 shows a schematic drawing of the spectral intensity of a phase and polarization shaped excitation pulse.

FIG. 11 exemplifies the spectral intensity of a phase and polarization shaped excitation pulse. According to this example, a $\pi$ phase-shifted gate 110 is introduced at a y polarization shifted band 111, serving as a probe. The probe is thus split into two spectrally distinct longer probe pulses with opposite phase. Due to the broad nonresonant spectral response, the nonresonant background from these two probe pulses interferes destructively. Since the $A_{xx}(\Omega)$ component of the amplitude is a very smooth function, these two probe pulses are almost equal in magnitude. As a result, the nonresonant background component of the CARS signal can be reduced by orders of magnitude.

Figure 12:
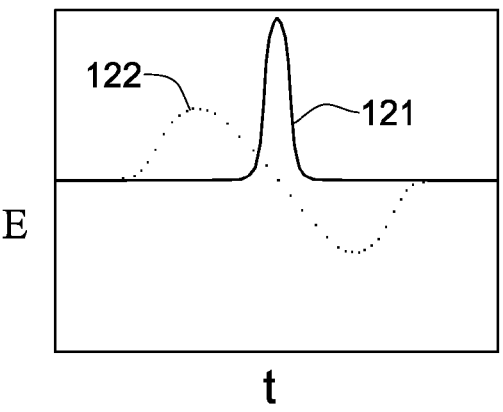
FIG. 12 is a schematic drawing of the electric field envelope versus time for phase and polarization shaped pulses.

This reduction can be alternatively viewed in time domain. FIG. 12 shows a schematic drawing of the electric field envelope versus time in both the x polarization (curve 121) and the y polarization (curve 122) for both phase and polarization shaped pulse. For convenience, the x polarization field has been reduced by about two orders of magnitude. As can be appreciated, the $\pi$ phase gate modifies the temporal shape of the y polarized probe so that the electric field envelope crosses zero at the peak of the x polarized driving field.

Due to the instantaneous nonresonant response, the nonresonant background is almost completely suppressed. The resonant signal response is different. It should be noted that the $\pi$ phase gate compensates for the sign inversion of the denominator in Eq. 9, leading to an increased resonant signal over a narrow spectral band shifted by the Raman level energy from the $\pi$ phase gate location.

Figure 13A:
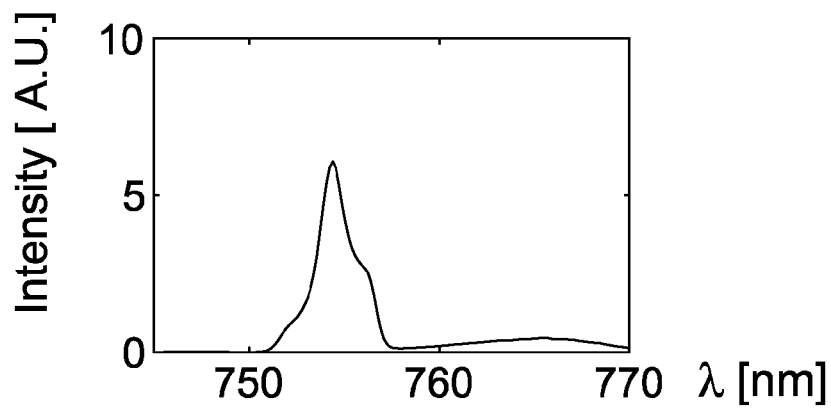
FIG. 13A to FIG. 13C illustrate CARS spectra from iodomethane obtained with both polarization and phase gate shaping and plotted for various probe bandwidths.
Figure 13B:
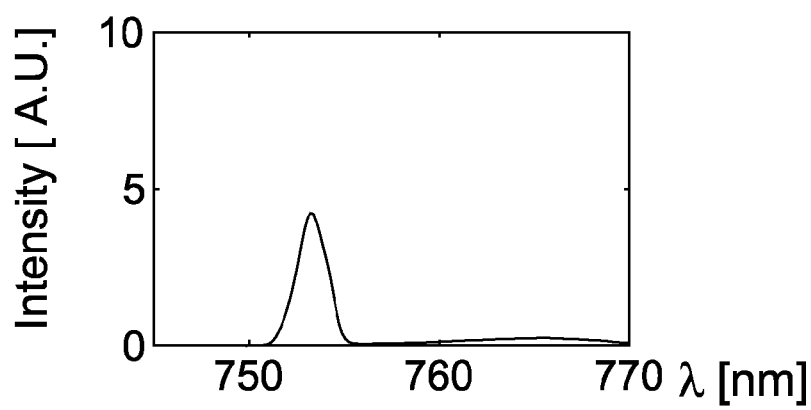
Figure 13C:
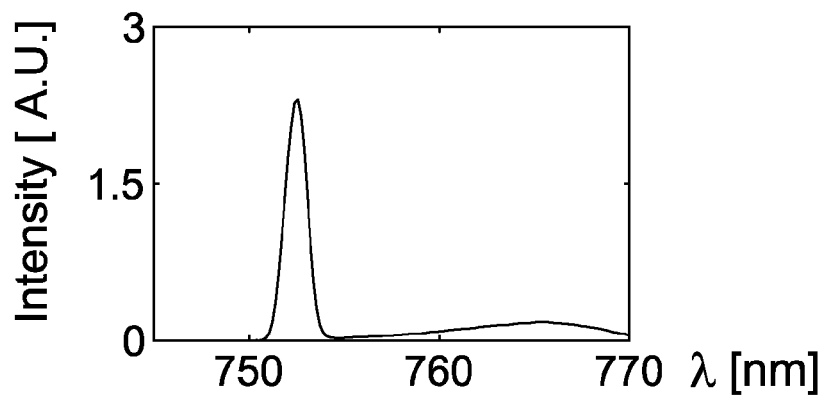

Referring to FIGS. 13A-13C, examples of the CARS spectra from iodomethane obtained with both polarization and $\pi$ phase gate shaping are plotted for various probe spectral bandwidths. According to this examples, the total probe bandwidth varies from 4.5 nm (for the example shown in FIG. 13A) to 2.4 nm (for the example shown in FIG. 13B), and then further to 1.2 nm (for the example shown in FIG. 13C). When the measured spectra obtained by using the polarization and phase shaped probe pulses (shown in FIGS. 13A-13C) are compared to the measured spectra obtained by using polarization-only shaped transform limited pulses (shown in FIGS. 10A-10D), a dramatic decrease in the nonresonant background can be seen. It should be noted that the small nonresonant background that is still observed using the phase-shaped probe is in fact a small fraction (about 0.05%) of the $\chi_{xxxx}$ component which "leaks" through the polarizer due to small birefringence of the microscope objective and collection optics. However, since this background component is independent on the applied phase and polarization, it can be easily subtracted.

Figure 14A:
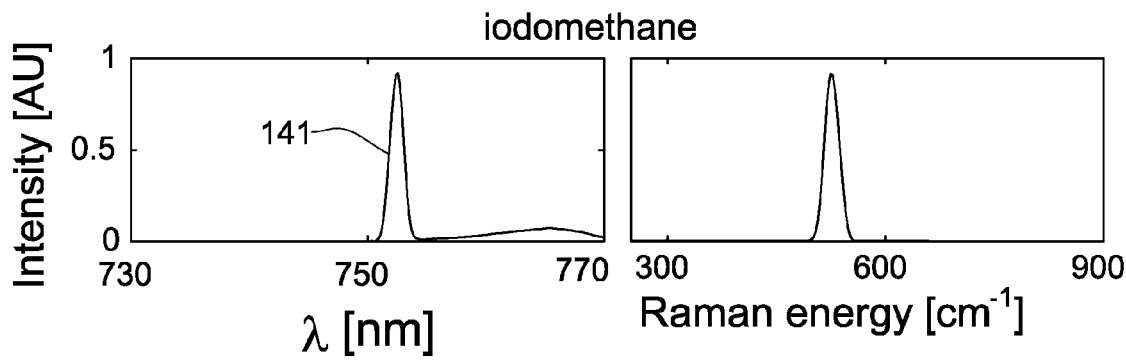
FIG. 14A to FIG. 14C illustrate examples of Raman spectra of several simple molecules obtained with phase and polarization shaped pulses.
Figure 14B:
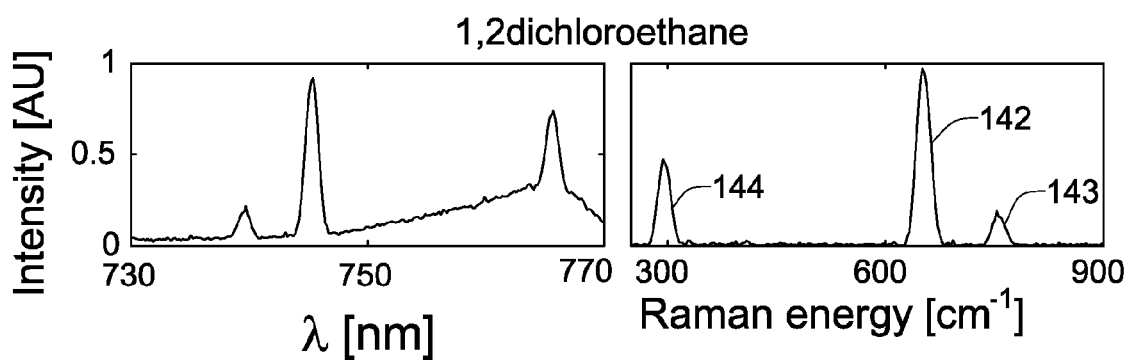
Figure 14C:
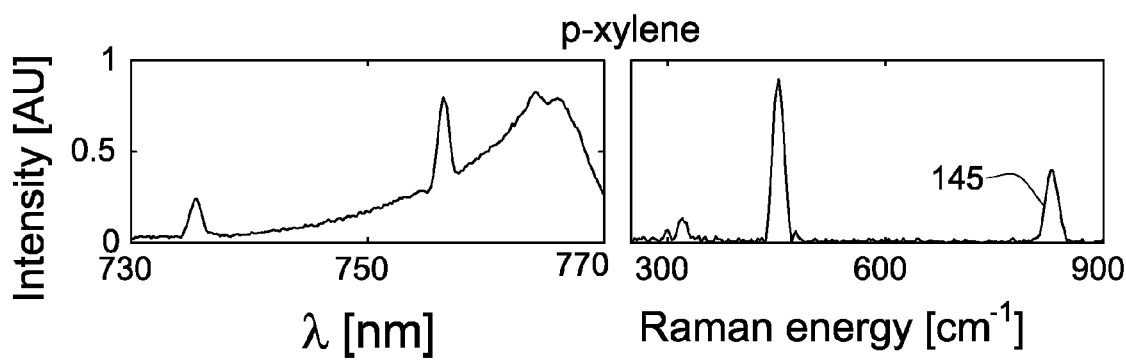

Referring to FIGS. 14A-14C, examples of Raman spectra of several simple molecules obtained with phase and polarization shaped pulses are illustrated. The total probe bandwidth has been about 1.2 nm, including a $\pi$ phase gate at the bandwidth's center. The "raw" measured CARS spectra are shown in the left part of the figures. It should be noted that the small nonresonant background that is still observed is in fact a small fraction (about 0.05%) of the $\chi_{xxxx}$ component which "leaks" through the polarizer due to small birefringence of the microscope objective and collection optics. Since this background component is independent on the applied phase and polarization, it can be easily subtracted. The extracted Raman spectra, from which the background due to birefringence was subtracted, are plotted on the right part of the figures.

FIG. 14A shows a peak 141 corresponding to the 523 cm$^{-1}$ Raman level of iodomethane. The full-width at half maximum of this peak is about 15 cm$^{-1}$.

The measured Raman spectrum of 1,2-dichloroethane is shown in FIG. 14B. The levels at 652 cm$^{-1}$ and 750 cm$^{-1}$, separated by 98 cm$^{-1}$ are seen as two very well separated peaks 142 and 143. This spectrum also has a peak 144 corresponding to the level at 298 cm$^{-1}$ located at the lower limit of the detectable region.

The Raman spectrum of p-xylene, having a peak 145 corresponding to the level at 830 cm$^{-1}$ is shown in FIG. 14C. This example demonstrates the ability of the technique of the present invention to observe the high-energy end of the detectable region. It should be noted that the measured energy range can be extended to higher frequencies (1000-15000 cm$^{-1}$) by using shorter pulses.

Figure 15:
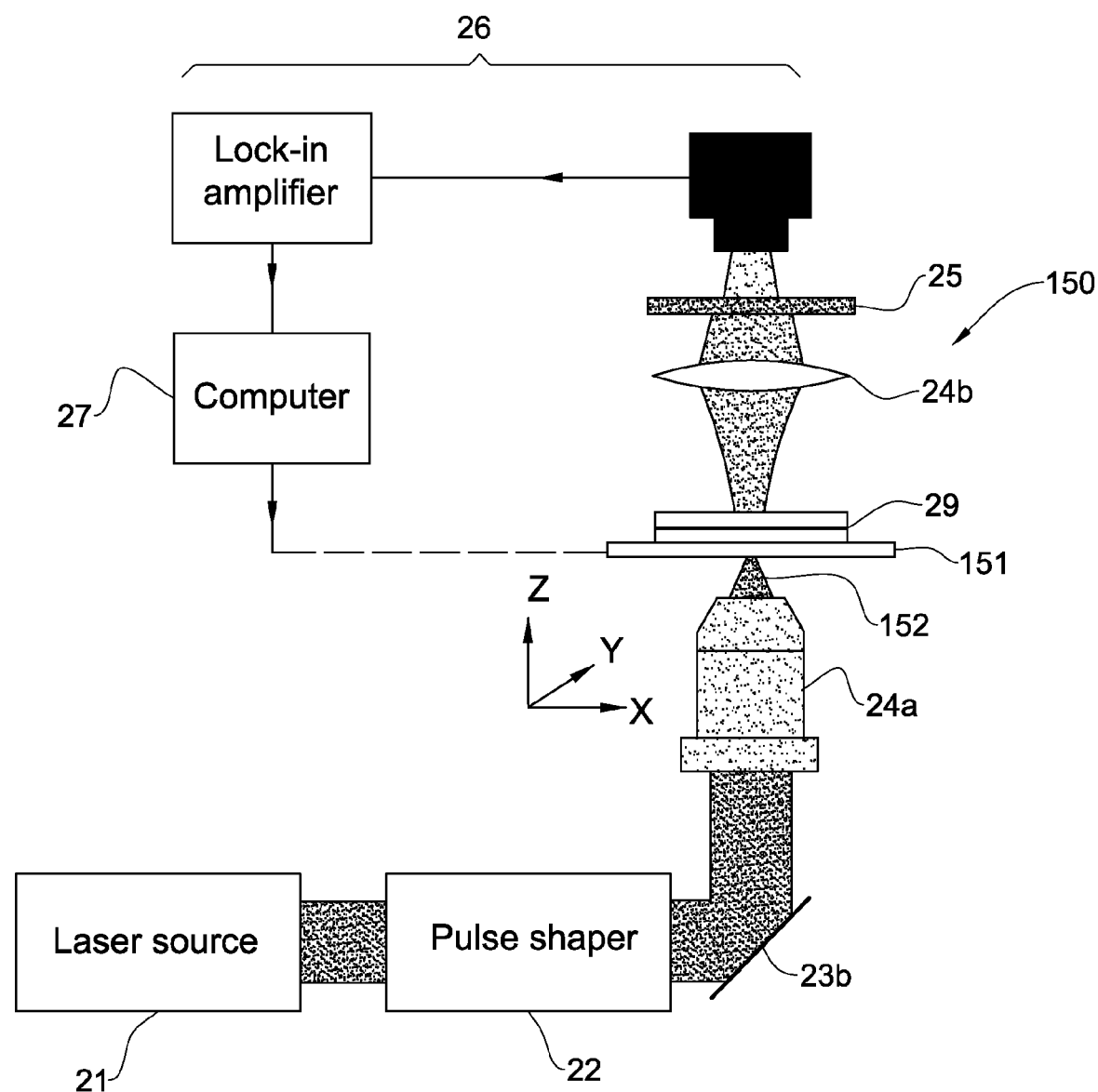
FIG. 15 illustrates a schematic view of a single-pulse CARS microscopy system, according to one embodiment of the invention.

Single-pulse CARS is particularly suitable for nonlinear microscopy. FIG. 15 exemplifies a single-pulse CARS microscope 150 according to the invention. Generally, the CARS microscope 150 includes all the elements of the single-pulse spectrometer (20 in FIG. 2A or 200 in FIG. 2B) needed for inducing a CARS process in the molecules of a target material and for detecting the CARS signal scattered by the material. More specifically, the CARS microscope 150 includes means for inducing the CARS process by producing a beam constituted of unitary optical excitation pulses and directing it through the target material placed on the sample holder 29. According to the technique of the present invention, each pulse is a unitary pulse that carries a pump photon, a Stokes photon and a probe photon. The CARS microscope thus includes a laser 21 adapted for generating at least one transform limited optical pulse and a programmable pulse shaper 22 (constituting a control means for coherently controlling the CARS process) operable for shaping the transform limited optical excitation pulse obtained from the laser 21, a detector unit 26, and a light directing optics. The shaping is carried out by correcting the pulse dispersion as well as assigning the desired phase (and, optionally, polarization) to the pulse, as described above.

The light directing optics of the CARS microscope 150 includes a focusing assembly (e.g., a microscope objective) 24a arranged for creation a focal spot 152 formed by the beam on the target material; a lens assembly 24b arranged for collecting the output CARS signal from the target material; and a filtering assembly 25 operable for filtering the collected output CARS signal propagating towards the detector unit 26. All these components are similar to those described above in connection with the CARS spectrometer system (20 in FIG. 2A or 200 in FIG. 2B).

The CARS microscope 150 utilizes scanning of at least a portion of the target material with the focal spot 152, which can be implemented by supporting the sample holder on a stage 151 driven for movement, and/or by mounting at least some of optical elements for movement with respect to the sample holder to thereby appropriately deflect the incident beam. The microscope objective 24a may for example be that commercially available from ZEISS. The stage driver may include a piezoelectric transducer, e.g., P-282 XYZ Nano positioners commercially available from Physik Instrumente (PI) GmbH.

An example of single-pulse spectrally resolved microscopy is demonstrated herein below. A selected target material was a glass capillary plate with 10-µm holes filled with $CH_2Br_2$ (having a resonant at 577 cm$^{-1}$). The sample was raster-scanned around the focused laser beam using computer-controlled piezoelectric drivers.

Figure 16A:
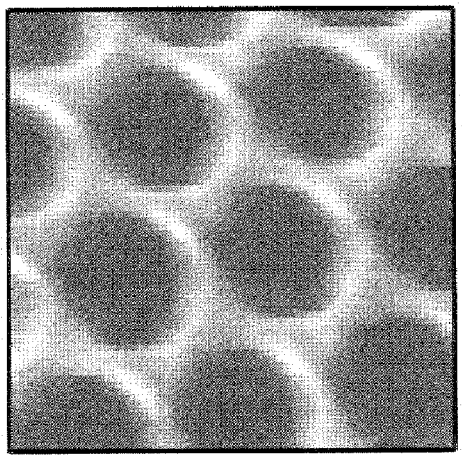
FIG. 16A to FIG. 16D illustrate an example of depth-resolved single-pulse CARS images.
Figure 16B:
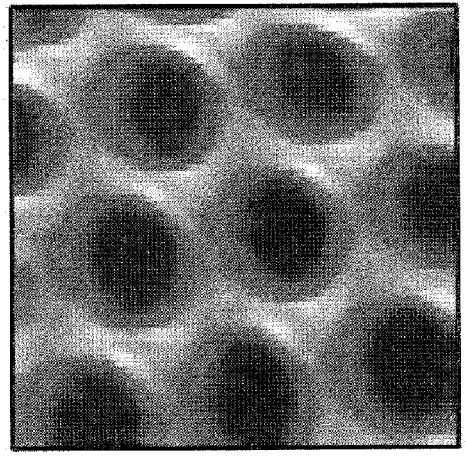

An image shown in FIG. 16A was taken with a pulse shape maximizing the relative intensity of the resonant contribution, whereas the image shown in FIG. 16B was taken with a pulse shape minimizing this intensity.

The predominantly resonant signal from the filled holes shown in FIG. 16A is larger by a factor of 4 than that in FIG. 16B, while the signals obtained from the glass is almost similar.

Figure 16C:
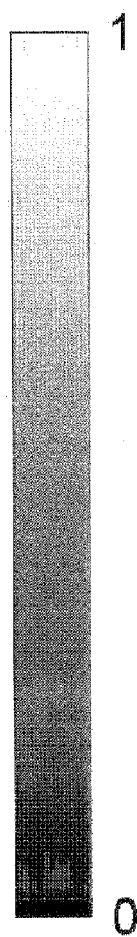
Figure 16C:
Figure 16D:
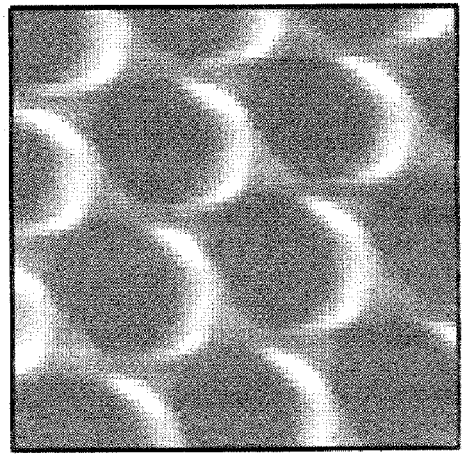

FIG. 16C shows an image that is a difference between the images in FIG. 16A and FIG. 16B, depicting the signal from the 577 cm$^{-1}$ vibrational level of $CH_2Br_2$. This image appears inverted relative to that obtained by using a transform-limited pulse (shown in FIG. 16D), where the glass, having a larger nonresonant signal, appears brighter. The image in FIG. 16C demonstrates the ability of the microscope to spectrally resolve the Raman resonant contribution of a single vibrational level. In a practical system, the difference image can be directly measured by lock-in detection, alternating the phase masks of the images shown in FIGS. 16A and 16B at a high frequency.

It should be appreciated that for materials having more than one vibrational level it is possible to improve the detection selectivity by tailoring shaped pulses to induce constructive quantum interference of these levels.

As such, those skilled in the art to which the present invention pertains, can appreciate that while the present invention has been described in terms of preferred embodiments, the concept upon which this disclosure is based may readily be utilized as a basis for the designing of other structures, systems and processes for carrying out the several purposes of the present invention.

Although the example of utilization of the CARS spectrometer technique of the present invention were shown for CARS microscopy, the spectral measurement utilizing the coherent control of the present invention can be easily combined with other nonlinear microscopic methods such as multiphoton fluorescence and third-harmonic generation using the same microscope system.

Also, it is to be understood that the phraseology and terminology employed herein are for the purpose of description and should not be regarded as limiting.

It is important, therefore, that the scope of the invention is not construed as being limited by the illustrative embodiments set forth herein. Other variations are possible within the scope of the present invention as defined in the appended claims and their equivalents.

The invention claimed is:

1. A method for use in inducing a Coherent Anti-Stokes Raman Scattering (CARS) signal from a medium, the method comprising shaping a unitary optical pulse carrying a pump photon, a Stokes photon and a probe photon and producing a unitary optical excitation pulse, said shaping comprising blocking a spectrum of the unitary optical pulse in an expected spectral range of the CARS signal, the method thereby enabling inducing and detection of the CARS signal from the medium by application of said unitary optical excitation pulse to the medium.

2. The method of claim 1, wherein said shaping of the unitary optical pulse comprises assigning a desired phase to each wavelength component of the unitary optical pulse, said assigning comprises modulating a spectral phase of the unitary optical pulse by using a desired spectral phase function, the spectral phase function being determined by a closed feedback loop, said shaping thereby producing said unitary optical excitation pulse.

3. The method of claim 1, wherein said shaping of the unitary optical pulse comprises assigning a desired phase to each wavelength component of the unitary optical pulse, said assigning comprises modulating a spectral phase of the unitary optical pulse by using a desired spectral phase function changing a symmetry of a polarization defining product E(ω−Ω)A(Ω) for different values ω around Ω=$Ω_R$, E(ω) being a spectrum of an electric field of the excitation pulse, A(Ω) being a probability amplitude to populate a vibrational level with energy $\hbar\Omega$, $\hbar\Omega_R$ being an energy of an intermediate level of a CARS transition.

4. The method of claim 1 wherein said shaping comprises passing the unitary optical pulse through a Spatial Light Modulator (SLM).

5. The method of claim 1 wherein said unitary optical pulse is in a range of about 5 to 100 femtoseconds.

6. The method of claim 1 comprising producing said unitary optical pulse.

7. The method of claim 1 wherein the shaping comprises splitting said unitary optical pulse into a broadband pump component and a narrow-band probe component having substantially orthogonal polarizations.

8. The method of claim 1, wherein the blocking is applied to wavelengths shorter than a long edge of the expected spectral range of the CARS signal.

9. The method of claim 6, said producing comprising providing a transform limited optical pulse.

10. The method of claim 7 wherein said broadband pump and narrow-band probe components are phase-controlled.

11. The method of claim 8 wherein said shaping of the unitary optical pulse comprises assigning a desired phase to each wavelength component of the unitary optical pulse, said assigning comprises modulating a spectral phase of the unitary optical pulse by using a desired spectral phase function, said desired spectral phase function being a periodic function.

12. The method of claim 11 wherein said desired spectral phase function is provided with an involvement of at least one phase gate having a bandwidth substantially narrower than a bandwidth of the unitary optical excitation pulse.

13. The method of claim 12 wherein at least one phase gate is a π phase gate.

14. The method of claim 13 wherein the bandwidth of said π phase gate is in a range of about 0.5 nm to 3 nm.

15. The method of claim 13 wherein said π phase gate is spectrally located within a short wavelength part of the unitary optical excitation pulse.

16. A system for use in inducing a Coherent Anti-Stokes Raman Scattering (CARS) signal from a medium, the system comprising a pulse shaper for accommodating in an optical path of a unitary optical pulse carrying a pump photon, a Stokes photon and a probe photon and being configured and operable to shape the unitary optical pulse into a unitary optical excitation pulse, the pulse shaper comprising a block element for blocking a spectrum of the unitary optical pulse in an expected spectral range of the CARS signal, and a programmable shaping assembly operable to modulate a spectral phase of the unitary optical pulse by a desired spectral phase function and assign a desired phase to each of the unitary optical pulse wavelength components.

17. The system of claim 16 comprising a closed feedback loop determining said spectral phase function.

18. The system of claim 16, wherein said spectral phase function changes a symmetry of a polarization defining product $E(\omega-\Omega)A(\Omega)$ for different values $\omega$ around $\Omega=\Omega_R$, $E(\omega)$ being a spectrum of an electric field of the excitation pulse, $A(\omega)$ being a probability amplitude to populate a vibrational level with energy $\hbar\Omega$, $\hbar\Omega_R$ being an energy of an intermediate level of a CARS transition.

19. The system of claim 16 wherein said programmable pulse shaping assembly comprises an input dispersive device for spatially separating wavelength components of the unitary optical pulse; a programmable Spatial Light Modulator (SLM) accommodated in the optical path of said separated wavelength components and operable to modulate said separated wavelength components by at least the desired spectral phase function; and an output dispersive device for recombining the modulated wavelength components into the unitary optical excitation pulse.

20. The system of claim 16 wherein the unitary optical pulse is in a range of about 5 to 100 femtoseconds.

21. The system of claim 16 wherein said desired spectral phase function is a periodic function.

22. A CARS spectrometer comprising the system of claim 16.

23. A CARS microscope comprising the system of claim 16.

24. The system of claim 16 comprising a single laser operable to generate at least one unitary optical pulse.

25. The system of claim 16 comprising a detector unit for receiving an output CARS signal produced by the medium excited by said unitary optical excitation pulse and generating data indicative thereof.

26. The system of claim 16, wherein said programmable pulse shaping assembly comprises a polarization control assembly operable to apply a polarization rotation to predetermined wavelength components of the unitary optical pulse and thereby produce a broadband pump component and a narrow-band probe component having substantially orthogonal polarizations, and to apply a cross polarization filtering to a signal propagating from the medium to a detector unit for extraction of the cross-polarized CARS signal.

27. The system of claim 16 comprising: a filtering assembly accommodated in the optical path of an output CARS signal propagating from the medium towards a detector unit, said filtering assembly being operable to apply a frequency filtering to said output CARS signal.

28. The system of claim 16 comprising at least one phase gate having a bandwidth substantially narrower than the bandwidth of the unitary optical excitation pulse.

29. The system of claim 24, said single laser being operable to generate a transform limited optical pulse.

30. The system of claim 24 wherein said single laser is a Ti:Sapphire laser.

31. The system of claim 25 wherein said detector unit includes a lock-in amplifier.

32. The system of claim 25, comprising light directing optics for directing the unitary optical excitation pulse to the medium and directing the output CARS signal to the detector unit.

33. The system of claim 26, wherein said polarization control assembly comprises an input polarization filtering unit accommodated in the optical path of the unitary optical pulse.

34. The system according to claim 26, wherein the polarization control assembly comprises a Spatial Light Modulator (SLM) arrangement.

35. The system of claim 27 wherein said filtering assembly includes at least one of the following: a bandpass filter, a short-pass filter; a spectrograph.

36. The system of claim 27 wherein said filtering assembly includes a monochromator.

37. The system of claim 28 wherein the phase gate is a $\pi$ phase gate.

38. The system of claim 37 wherein the bandwidth of said $\pi$ phase gate is in a range of about 0.5 nm to 3 nm.

39. The system of claim 37 wherein said $\pi$ phase gate is spectrally located within a short wavelength part of the excitation pulse.

* * * * *